(12) United States Patent
Swope et al.

(10) Patent No.: US 9,622,456 B2
(45) Date of Patent: Apr. 18, 2017

(54) DEVICE AND METHOD FOR ANIMAL IDENTIFICATION

(71) Applicant: RapID Lab, Inc., San Francisco, CA (US)

(72) Inventors: Bretton Mark Swope, San Francisco, CA (US); Eric Malcomb Ibsen, San Francisco, CA (US)

(73) Assignee: RapID Lab, Inc., San Francisco, CA (US)

( * ) Notice: Subject to any disclaimer, the term of this patent is extended or adjusted under 35 U.S.C. 154(b) by 48 days.

(21) Appl. No.: 14/614,328

(22) Filed: Feb. 4, 2015

(65) Prior Publication Data

US 2015/0148811 A1 May 28, 2015

Related U.S. Application Data

(63) Continuation of application No. 14/042,663, filed on Sep. 30, 2013, now abandoned, which is a continuation of application No. 12/589,119, filed on Oct. 15, 2009, now abandoned.

(51) Int. Cl.
*A61B 17/00* (2006.01)
*A01K 11/00* (2006.01)
*A61B 17/34* (2006.01)

(52) U.S. Cl.
CPC .......... *A01K 11/004* (2013.01); *A01K 11/001* (2013.01); *A01K 11/002* (2013.01); *A61B 17/3468* (2013.01)

(58) Field of Classification Search
CPC ..... A01K 11/00–11/004; A01K 13/003; A61B 17/3468

USPC .................. 606/117, 188, 184; 40/300, 301; 227/143–144; 206/338–340
See application file for complete search history.

(56) References Cited

U.S. PATENT DOCUMENTS

| 4,368,735 A | * | 1/1983 | Filmer | A01K 11/002 227/144 |
| 6,439,169 B1 | * | 8/2002 | Miyawaki | A01K 11/004 119/655 |
| 2004/0103568 A1 | * | 6/2004 | Steinfort | A01K 11/00 40/301 |

FOREIGN PATENT DOCUMENTS

DK    WO 2008044219 A2 *  4/2008  .......... A01K 11/001

* cited by examiner

*Primary Examiner* — Melanie Tyson
*Assistant Examiner* — Erich Herbermann
(74) *Attorney, Agent, or Firm* — Run8 Patent Group; Peter Miller

(57) ABSTRACT

Methods and device for marking animals are disclosed. An ear tag configurable for attachment to a rodent ear, e.g., a mouse ear, is presented, wherein the ear tag includes a color-coded image, an alphanumeric character string, a bar code and/or a visual signage. The tag may include the visual identifier and an RFID device. A card may be provided that redundantly displays some or all of the visual identifier. An applicator is alternately or additionally provided that removes separated elements of the tag from a tray force generated by manual compression of a pair of handles of the applicator, and additionally includes jaws that compress towards each other when the handles are initially compressed, yet splay and release the tag elements as additional compressive force is applied to the handles.

18 Claims, 30 Drawing Sheets

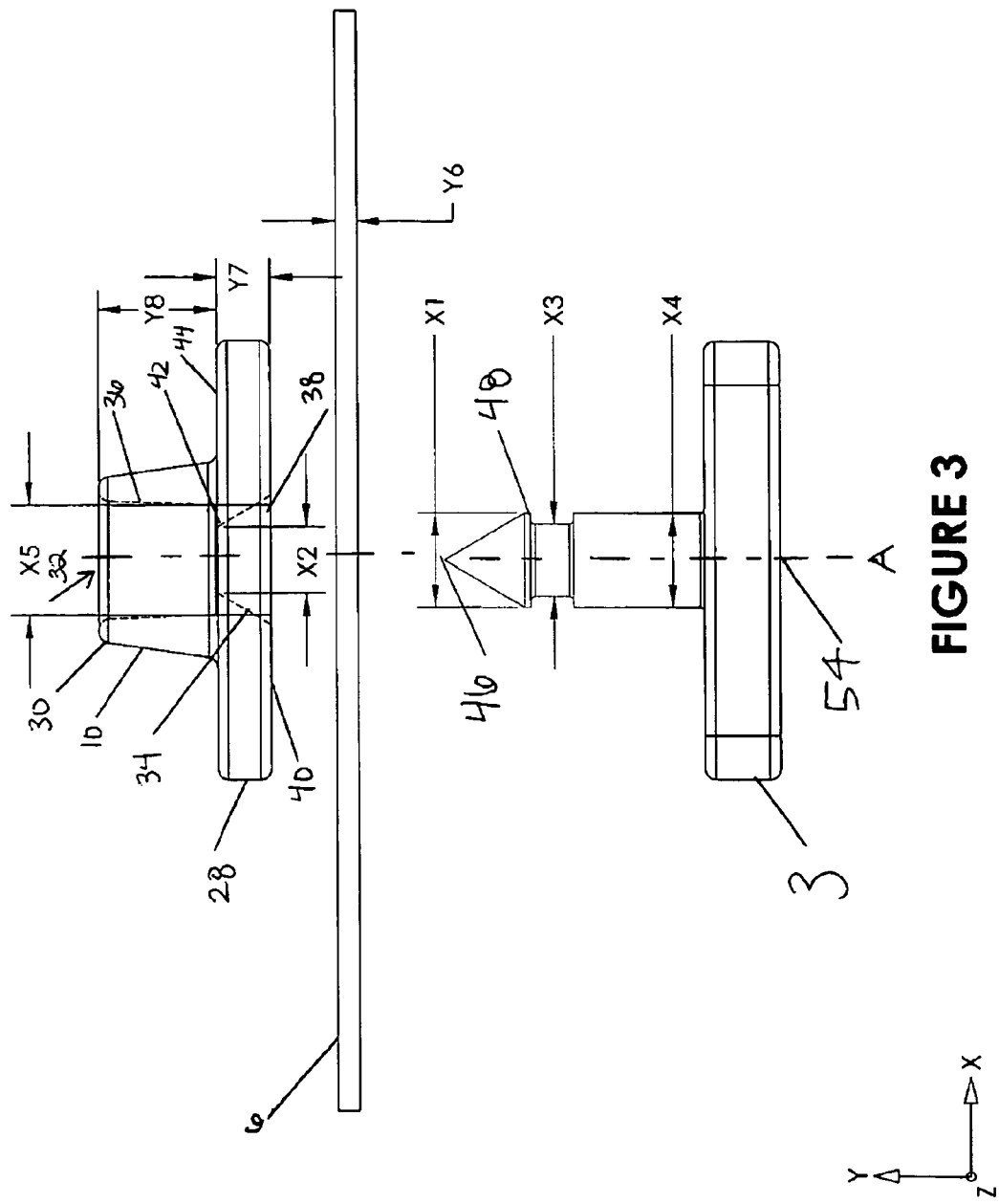

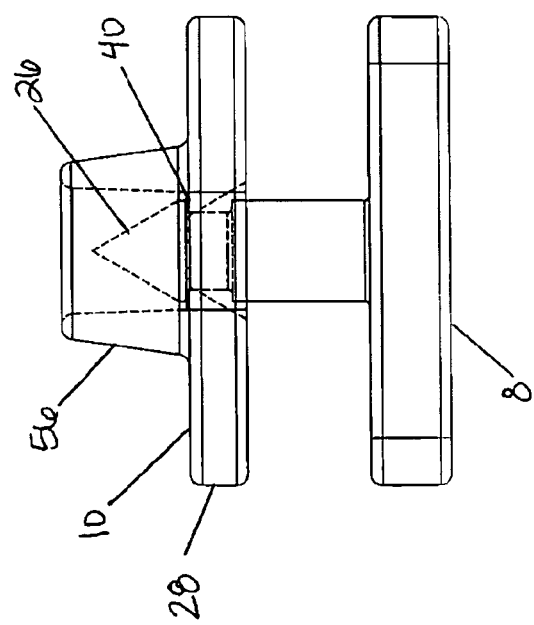
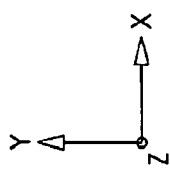
FIGURE 5

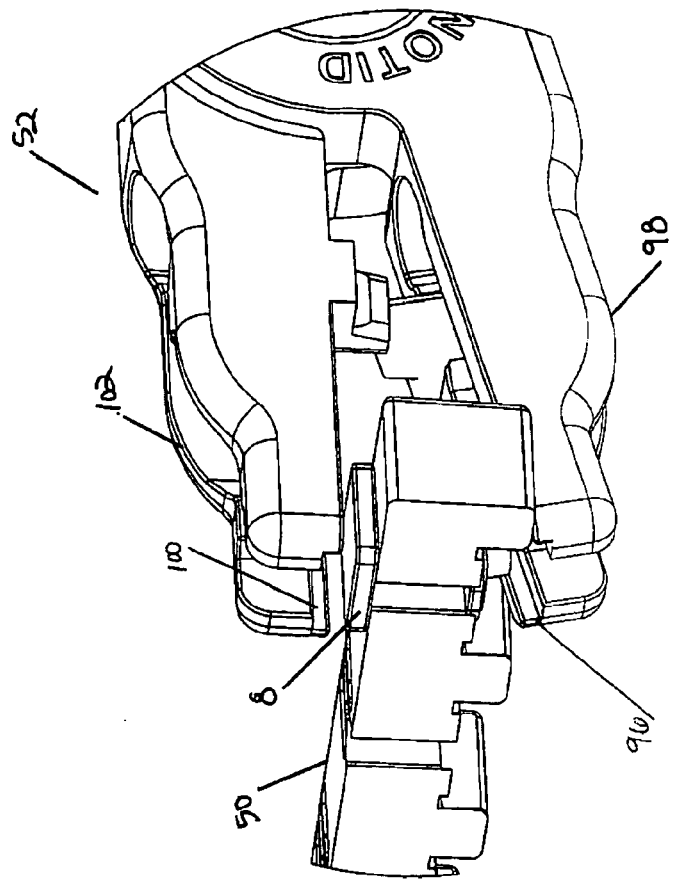
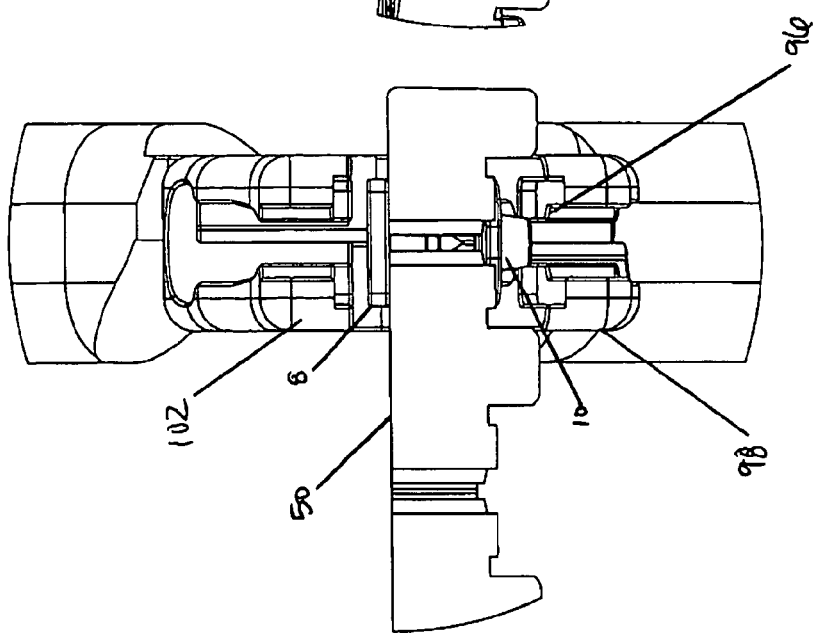
FIGURE 23B
FIGURE 23A

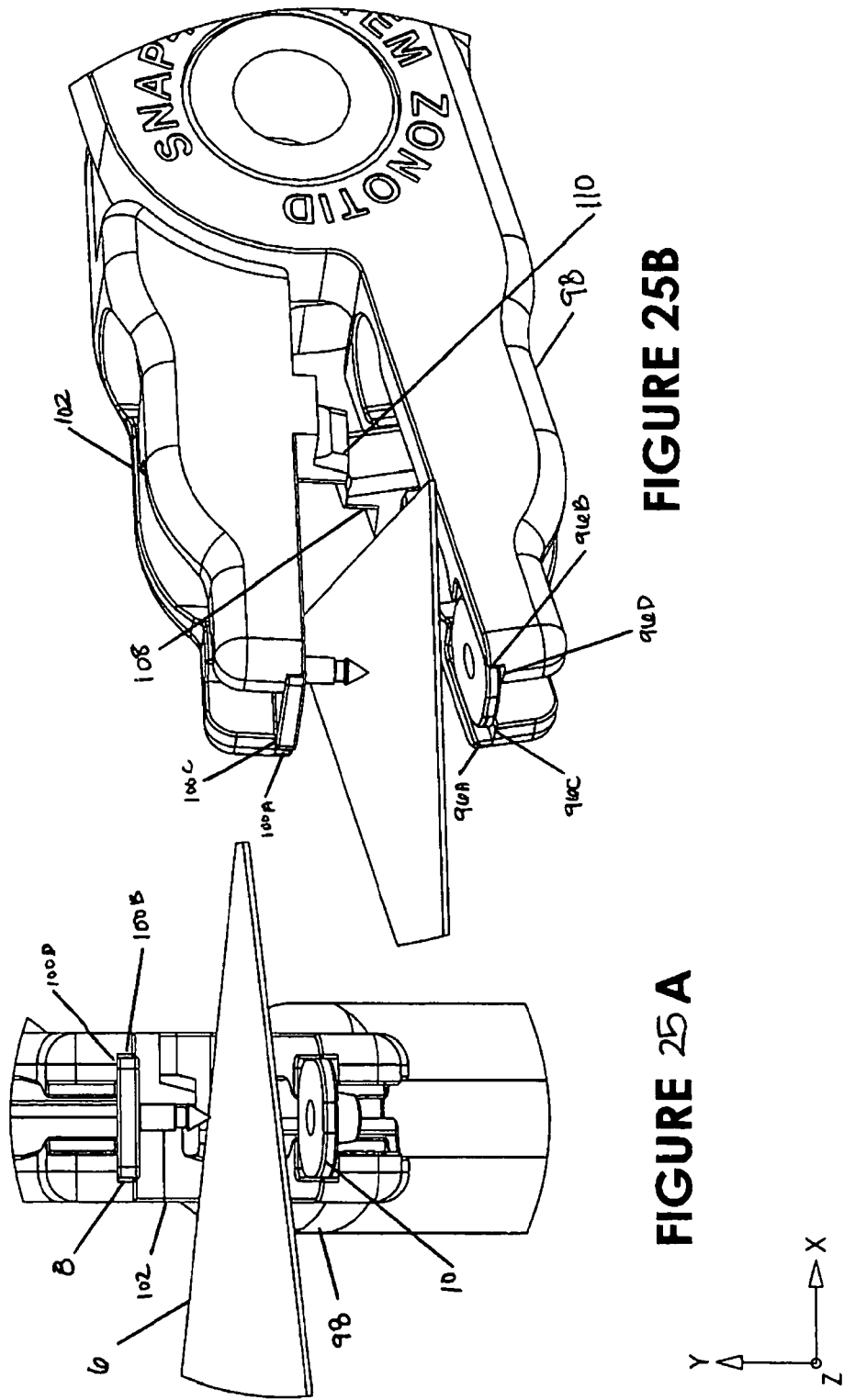

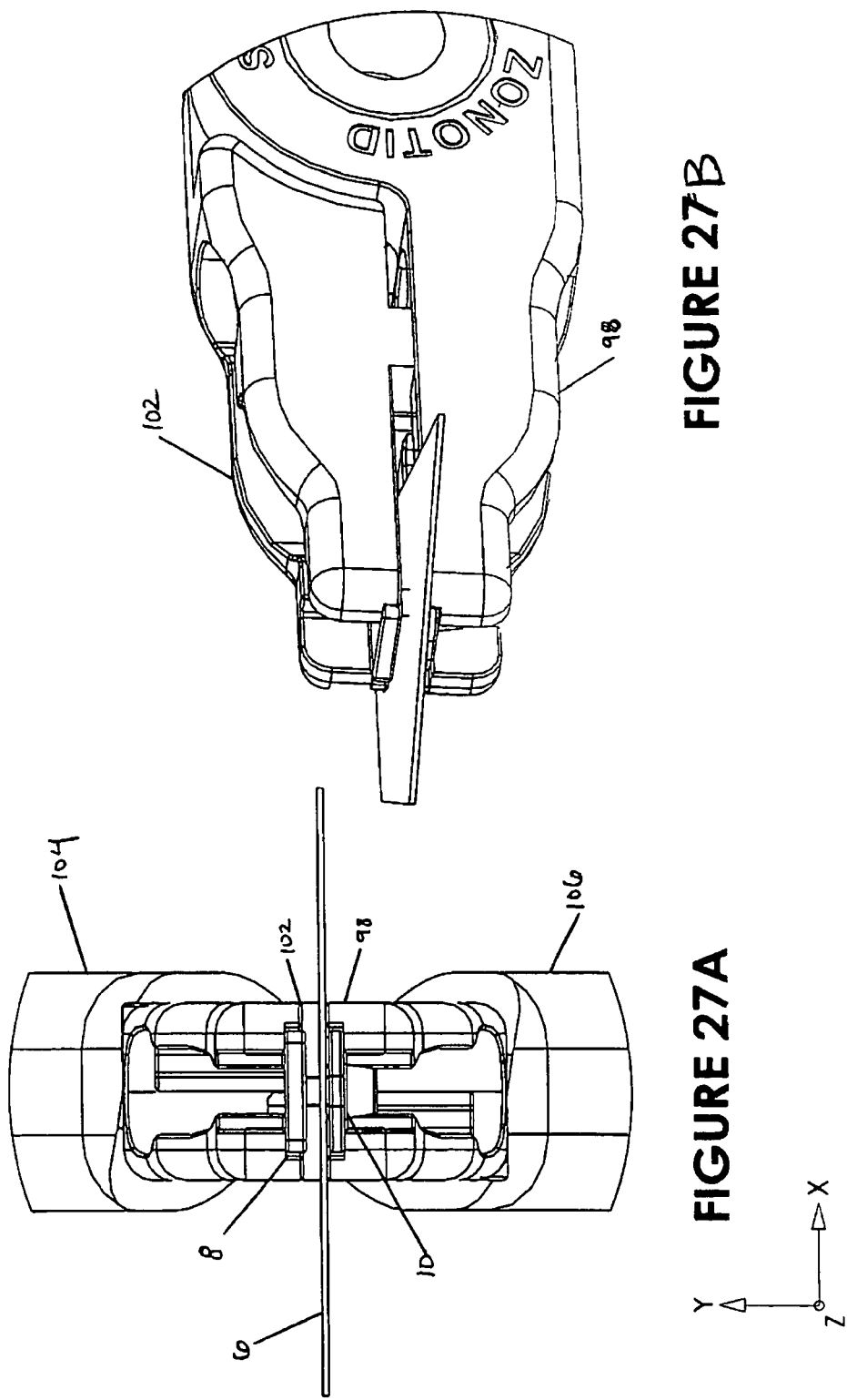

DEVICE AND METHOD FOR ANIMAL IDENTIFICATION

CROSS-REFERENCE TO RELATED APPLICATIONS

This application is a continuation application of U.S. patent application Ser. No. 14/042,663, filed on 30 Sep. 2013, which is a continuation application of U.S. patent application Ser. No. 12/589,119, filed on 15 Oct. 2009, both of which are incorporated in their entireties by this reference.

FIELD OF THE INVENTION

The present invention relates to the field of animal husbandry and research. More particularly, the present invention relates to marking animals for individual identification.

BACKGROUND OF THE INVENTION

Animals in both agricultural and research settings are often marked for management and control. Prior art methods for identifying small research animals include attaching metal ear tags and employing implanted or ingested electronic tags. Prior art metal ear tags are associated with host animal tissue reaction, tissue irritation, cancer incidence, other host animal health degradation and/or deformation of the host animal ear due to relatively high weight of the metal ear tag. In addition, prior art metal ear tags can induce host animal efforts to dislodge the ear tag that can result in damage to the animal itself and/or the ear tag.

The prior art includes transponder tags with radio frequency identification devices, or "RFID". Reading a radio frequency identification device requires the use of an RFID reader, i.e. an electronic device that communicates through wireless transmission with the RFID device. The RFID tag, passively responsive to an excitation signal transmitted from the RFID reader, can communicate coded information from the RFID transponder tag to the RFID reader, which then receives and decodes the information. Prior art implanted or ingested electronic tags are limited by their need to reflect or transmit a stream of data (e.g. their unique identification numbers) to the outside world. This requires relatively expensive transponder and receiver hardware and an invasive and risky surgical implantation process. Additionally, due to an inability to differentiate the identification number signal from two or more adjacent animals with passive RFID tags, animals must be first separated from one another or removed from the cage prior to scanning the animal. Animals which are group housed may not be scanned while within the cage because there is no way to direct the scanning area of the reader and identify a specific animal with certainty. It is preferable to scan group-housed animals without first removing them from their cage.

While animals are currently tagged with radio frequency identification devices in the prior art, it is often preferable that individual identification of a specific animal could be easily distinguished by a technician or laborer without the use of electronic or optical equipment. In addition, particularly when the animals of interest have modestly sized ears, such as mice bred for scientific research, it is preferable that a tag attached to an animal be of minimal discomfort or irritation to the host animal. It is also preferable for identifying markings to be readily visible, observable, or accessible, yet also verifiable or certifiable.

There is therefore an unmet need to provide a device and method that enables a reliable visual distinction of an animal by a laboratory researcher or animal caretaker.

SUMMARY OF THE INVENTION

Methods and systems for identifying animals are provided. According to a first aspect of the method of the present invention, a device is provided that displays a visual identifier. The visual identifier is optionally a color-coded image, an alphanumeric character string, a bar code and/or a signage. According to a second optional aspect, a tag includes the visual identifier and an RFID device. According to a third optional aspect, a card and/or sticker is provided that redundantly displays some or all of the visual identifier.

An applicator is alternately or additionally provided that removes the tag components from a tray by compression of a pair of handles, and additionally includes jaws that compress towards each other when the handles are initially compressed, yet separate away from each other as additional compressive force is applied.

The foregoing and other objects, features and advantages will be apparent from the following description of aspects of the present invention as illustrated in the accompanying drawings.

INCORPORATION BY REFERENCE

All publications mentioned herein are incorporated herein by reference to disclose and describe the methods and/or materials in connection with which the publications are cited. All publications, patents, and patent applications mentioned in this specification are herein incorporated by reference in their entirety and for all purposes to the same extent as if each individual publication, patent, or patent application was specifically and individually indicated to be incorporated by reference.

Such incorporations include U.S. Pat. No. 6,226,911 (Inventor: Wescombe; Issued on May 8, 2001) titled "Tag"; U.S. Pat. No. 6,098,324 (Inventor: Nepote; Issued on Aug. 8, 2000) titled "Animal identification device and method of manufacture"; and U.S. Pat. No. 7,533,482 (Inventor: Huenefeld, Issued on May 19, 2009) titled "Metal ear tag with electronic identification device".

The publications discussed or mentioned herein are provided solely for their disclosure prior to the filing date of the present application. Nothing herein is to be construed as an admission that the present invention is not entitled to antedate such publication by virtue of prior invention. Furthermore, the dates of publication provided herein may differ from the actual publication dates, which may need to be independently confirmed.

BRIEF DESCRIPTION OF THE FIGURES

These, and further features of various aspects of the present invention, may be better understood with reference to the accompanying specification, wherein:

FIG. 3 is a dimensioned side view of the receiver and the rivet of FIGS. 1, 2A and 2B positioned respectively on either side of an animal's ear;

FIG. 5 is a side view of the tag of FIGS. 1 through 4 and wherein the post tip of the first tag has extended into a protective channel of the receiver of FIGS. 1 and 3 through 4;

FIG. 23A is a front view of the applicator of FIGS. 12 through 21 engaging with the tray of FIGS. 8A through 12 and FIGS. 15 through 17;

FIG. 23B is a perspective view of the applicator of FIGS. 12 through 21 and FIG. 23A approaching the tray of FIGS. 8A through 12 and FIGS. 15-17 but not touching the first tag of FIG. 1 through 8, 11, 12, and FIGS. 14 through 20;

FIG. 25A is a front view of the applicator of FIGS. 12 through 21, 23, 24A and 24B positioned proximate to the ear of FIGS. 3, 4, 18, and 19;

FIG. 25B is a perspective view of the applicator of FIGS. 12 through 21 and 25A positioned proximate to the ear of FIGS. 3, 4, 18, 19, 20, and 25A;

FIGS. 23A through 26A is piercing the ear of FIGS. 3, 4, 18, 19, 20, 25A, 25B and 26A;

FIG. 27A is a front view of the applicator of FIGS. 12 through 21 and FIGS. 25A through 26B wherein the rivet jaw and the receiver jaw of the applicator are being pressed together by a compressing force delivered by the user to a first handle and a second handle of FIG. 17;

FIG. 27B is a perspective view of the applicator of FIGS. 12 through 21 and FIGS. 25A through 27A, wherein the rivet jaw and the receiver jaw of the applicator are being pressed together by a compressing force delivered by the user to the first handle and the second handle of FIG. 17;

DETAILED DESCRIPTION

It is to be understood that this invention is not limited to particular aspects of the present invention described, as such may, of course, vary. It is also to be understood that the terminology used herein is for the purpose of describing particular aspects only, and is not intended to be limiting, since the scope of the present invention will be limited only by the appended claims.

Methods recited herein may be carried out in any order of the recited events, which is logically possible, as well as the recited order of events.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
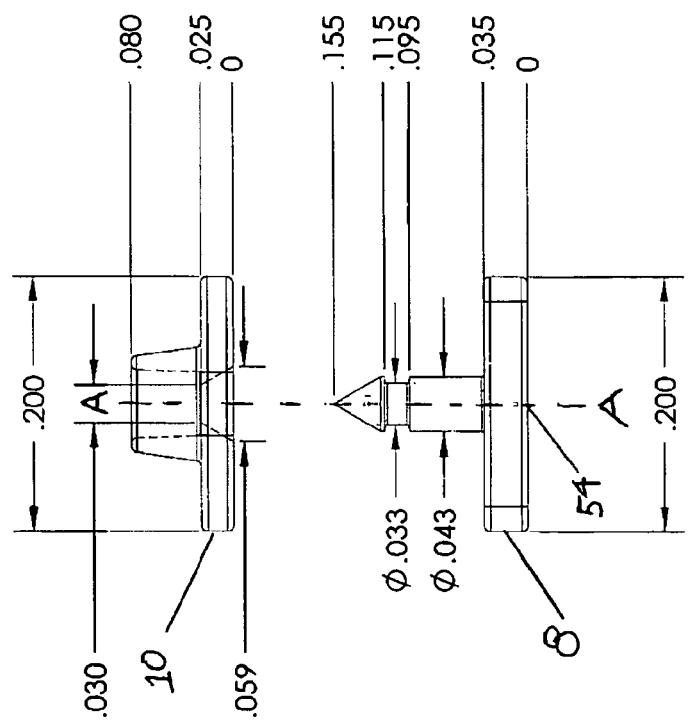
FIG. 1 is a side view of a first tag comprising a receiver and a rivet with preferred dimensions.

Referring now to FIG. 1, FIG. 1 is a side view of a first preferred alternate embodiment of the present invention, or first tag 2. The first tag 2 is configured for an attachment to a host animal 4 (as pictured in FIG. 7) weighing approximately 40 pounds or less. The host animal 4 may be an animal selected from, but not limited to, the group including a rodent, a mouse, a rat, a *felis domesticus*, a mole, a vole, an opossum and a rabbit.

Figure 7:
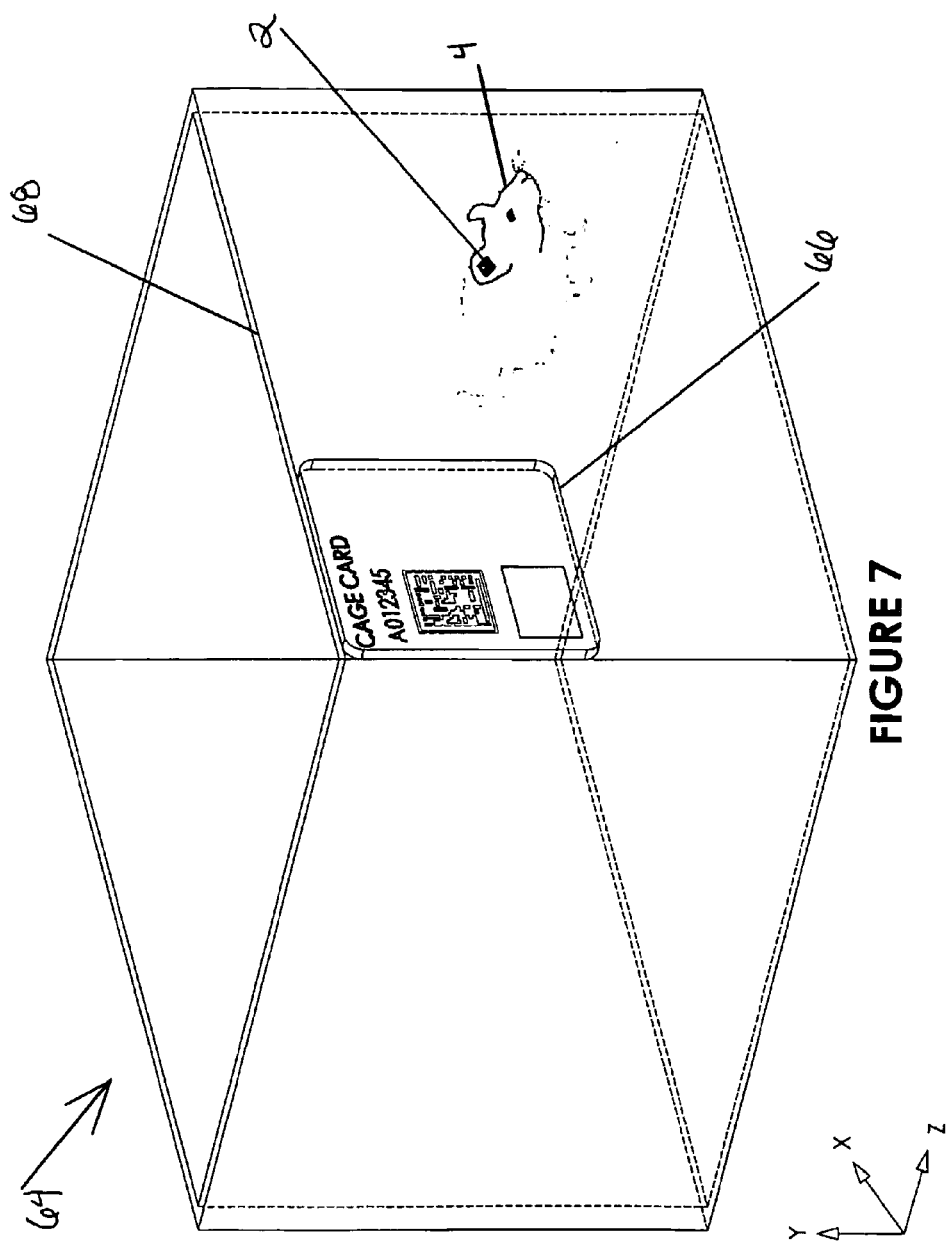
FIG. 7 is a perspective view of the tag of FIGS. 1 through 6 as coupled to a rodent's ear, wherein the rodent is housed within a cage bearing a cage card.

The first tag 2 preferably weighs less than 160 milligrams; more preferably weighs less than 100 milligrams; and most preferably weighs less than 60 milligrams. The reduced weight of the tag 2 in comparison to the prior art results in less discomfort to a host animal 4 (as shown in FIG. 7) to which the tag 2 is coupled, and reduces the possibility of damage to an ear 6 to which the tag 2 is coupled.

The first tag 2 includes a display rivet 8 and a receiver 10. An optional RFID 12 may be comprised within the display rivet 8 or the receiver 10. The RFID 12 may be a Nonatec™ radio frequency identification device marketed by Lutronic International of Rodange, Luxembourg or other suitable transponder known in the art.

The display rivet 8 preferably weighs less than 80 milligrams; more preferably weighs less than 60 milligrams; and most preferably weighs less than 40 milligrams. The display rivet 8 is composed of a rivet plate 14 and a rivet post 16. The rivet plate 14 includes a display plate 18 that extends within a display plane D defined as parallel to both the X axis and the Z axis. The display plate 18 may be affixed to the rivet plate 14 by an adhesive 20, or by other suitable means known in the art.

The display rivet 8 and receiver of the first tag 2 may be or comprise polyetheretherketone or other suitable organic or inorganic polymer(s) or plastic or ceramic material(s) or metal or metal alloy materials known in the art. Alternatively or additionally, the display plate 18 may comprise or consist of organic or inorganic polymer(s), metal, a metal alloy, titanium, stainless steel, ceramic or other suitable material known in the art that is resistant to damage from animal teeth or animal claws. It is understood that materials, such as titanium and polymers, that do not impair the effectiveness of medical imaging equipment such as magnetic resonance imaging, are preferably used to form the invented tag 2 in certain applications of the method of the present invention.

Inventively limiting the inclusion of metal to the display plate 18 of the invented tag 2, and the inventive use of selected plastics, e.g., polyetheretherketone, to substantially form the tag structure 2 avoids a potential for dermal irritation to a host animal 4 that may be caused by the use of a predominantly metal tag. In addition, the incidence of host animal cancer attributable to the use of prior art metal tags may also be reduced by limiting the use of metal to the display plate of the invented tag.

The inventive use of a lower density material, such as polyetheretherketone or other plastic, results in a tag 2 that has a lighter weight than a predominantly metal tag and minimizes a potential for damage and deformation. The inventive structure of the tag 2 lacks a loop and avoids a potential for host animal 4 claws dislodging as with prior art metal tags. The inventive inclusion of a thin strip of metal as, or within, the display plate 18 in certain preferred embodiments of the present inventions adds durability to the tag 2 and reduces damage that could potentially be inflicted by cohabitating animals that have access to the tag 2 as coupled with the host animal 4.

The receiver 10 and the rivet 8 may further comprise a dye material or colored substance that causes the receiver 10 and rivet 8 to present a same color visible to the human eye, such as red, blue, yellow, orange, green, purple.

Alternatively, the receiver 10 and the rivet 8 may further comprise a dye material or colored substance that causes the receiver 10 and rivet 8 to present a different visible color. For example, the receiver 10 may be red in color and the rivet 8 may be blue, yellow, orange, green or purple. Alternatively or additionally, the display plate 18 of the rivet 8 may present a color different from the remainder of the rivet 8, such as when the display plate 18 comprises titanium or other material different than that comprised within the rivet post 16 and remainder of the rivet 8.

The rivet post 16 preferably extends substantially normally from the display plane D of the plate along a central axis A, wherein the central axis A is parallel to a Y-axis and extends through the display plate 18 at a central point of the display plate 18. It is understood that the X-axis, the Y-axis and the Z-axis are each mutually orthogonal to the two other axes of the group of three axes.

The structure of the rivet post 16 includes a first cylindrical element 22, a second cylindrical element 24 having a smaller circular cross-sectional circumference than the circular cross-sectional circumference of the first cylindrical element 22, and a cutting tip 26.

The receiver 10 preferably weighs less than 80 milligrams; more preferably weighs less than 60 milligrams; and most preferably weighs less than 40 milligrams.

The receiver 10 comprises a receiver plate 28 and a collar 30, wherein a central circular channel 32 is defined by the receiver 10 to accept, protect and retain the rivet tip 26. The central channel 32 extends along the central axis A and is circular in a cross-sectional area parallel to the display axis D. The central channel 32 is defined by a combination of a circular angled channel 34 that extends fully through the receiver plate 28 and a circular protective channel 36 that extends from the receiver plate 28 and fully through the collar 30. The circular angled channel 34 extends from a first proximate diameter 38 located at a first side of the receiver plate 40 and narrows to a second distal diameter 42 located at a second side of the receiver plate 44, whereby the rivet tip 26 may be captured after passing fully through a location of the distal second diameter 42 of the angled channel 34 as located on the second side 44 of the receiver plate 28. When the rivet tip 26 is fully inserted through the angled channel 34 and is thereby captured by the receiver plate 28 and protected by the collar 30, the second cylindrical element 24 maintains the rivet plate 14 within a range of distance from the receiver plate 28, wherein the rivet display plate 18 is positioned distally from the receiver 10 and made available for visual observation.

The first tag 2 is presented in FIG. 1 with indications of exemplary physical dimensions. In particular, referring now to FIG. 1 and to FIG. 2A, the exemplary display plate 18 has a display thickness Y1 of 0.002 inches that is included of the exemplary rivet plate 14 thickness Y2 of 0.035 as measured along the central axis A of 0.035 inches, and both the exemplary display plate 18 and the comprising rivet plate 14 have a cross sectional area along the display plane D of 0.200 inches by 0.200 inches. The rivet post 16 extends from the rivet plate 14 to a total height of 0.155 inches along the central axis A. The first cylindrical element 22 of the rivet post 16 extends for 0.060 inches along the central axis A and presents a cross-sectional circular area having a diameter of 0.043 inches measured in parallel to the display plane D. The second cylindrical element 24 of the rivet post 16 is disposed between the first cylindrical element 22 and the tip 26 and extends for 0.020 inches along the central axis A. The second cylindrical element 24 presents a cross-sectional circular area having a diameter of 0.033 inches measured in parallel to the display plane D. The tip 26 of the rivet post 16 extends from the second cylindrical element 24 for 0.040 inches along the central axis A and is angled to a pointed end 46 of the cutting tip 26 from a lower tip diameter 48 of 0.043 inches as measured in parallel with the display plane D.

In certain alternate preferred embodiments of the method of the present invention, the cross-sectional area of the orthogonal rivet plate 14 normal to the central axis A is be in the range from two millimeters by two millimeters to ten millimeters by ten millimeters. Alternatively or additionally, in certain other alternate preferred embodiments of the method of the present invention, the cross-sectional area of the orthogonal receiver plate 28 is in the range from two millimeters by two millimeters to ten millimeters by ten millimeters.

It is understood that it is preferable that the receiver plate 28 and the rivet plate 14 each present a square shape in order allow the easier engagement of the first tag 2 with both the tray 50 and the applicator 52 as described below.

The receiver plate 28 has a thickness along the central axis A of 0.025 inches, and a preferably square cross sectional area parallel to the display plane D of 0.200 inches by 0.200 inches. The angled circular channel 34 of the receiver plate 28 opens at the first diameter 38 of 0.059 inches and narrows to the second narrower diameter 42 of 0.030 inches. The tip 26 of the rivet post 16 may be captured by presenting a lower tip diameter 48 larger than the second diameter 42 of the angled channel 34 of the receiver plate 28. As presented in FIG. 1, the exemplary rivet tip 26 presents a lower tip diameter 48 of 0.043 inches and the narrower second diameter 42 of the angled channel 34 presents a diameter of 0.030 inches.

It is understood that after the tip 26 has been forced fully through the narrower second diameter 42 of the angled channel 34 of the receiver plate 28, the tip 26 is thereafter impeded from removal through the angled channel 34 of the receiver plate 28.

In a forcing of the tip 26 through the receiver plate 28, the tip 26 and the receiver plate 28 plastically deform to allow the tip 26 to pass fully through the receiver plate 28. Some of this deformation of the tip 26 and the second diameter 42 is recovered after the tip 26 penetrates the receiver plate 28 and the interference between the tip 26 and the receiver plate 28 restored. This interference thereby captures the tip 26 inside the receiver 10.

Figure 2A:
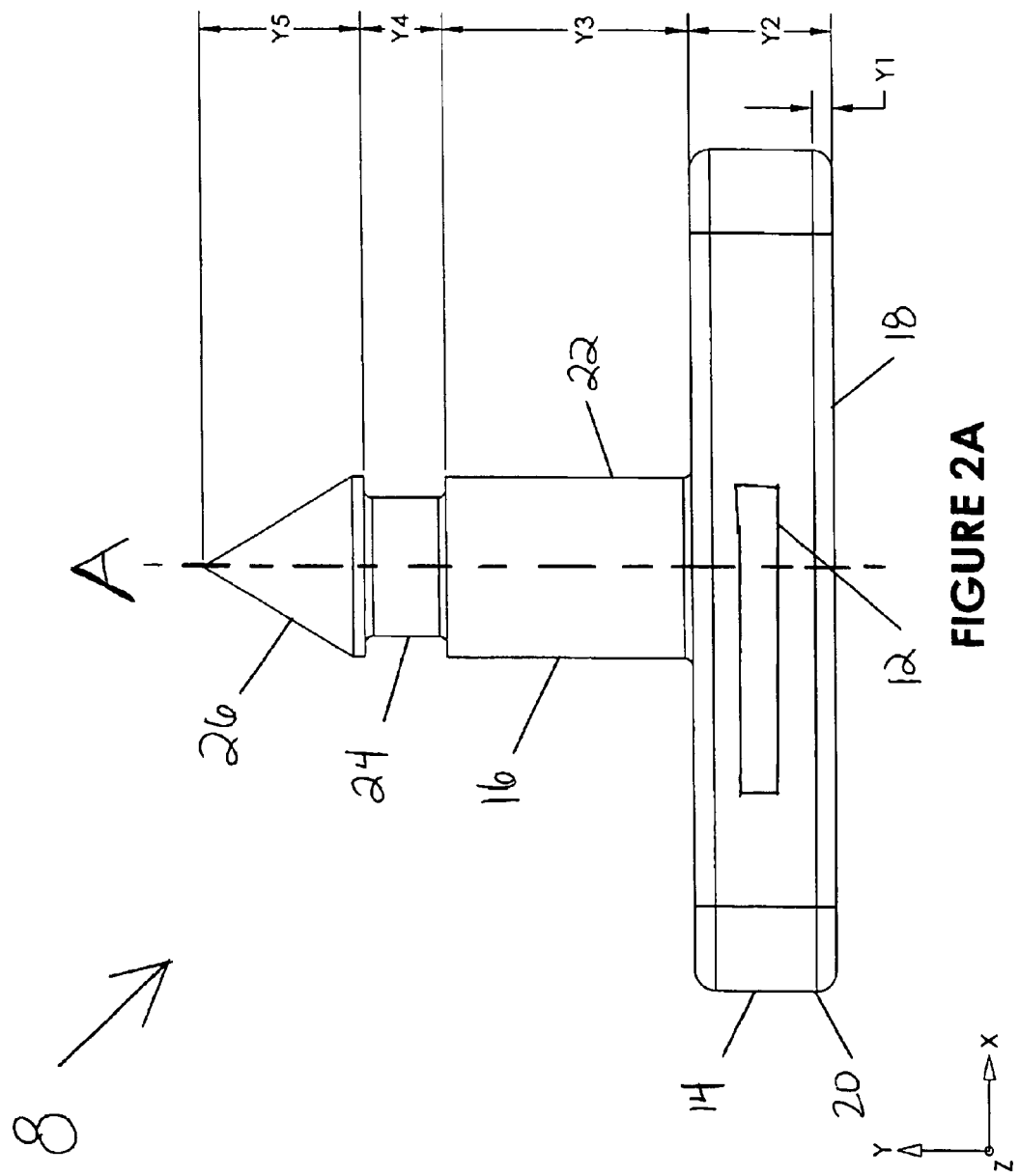
FIG. 2A is a dimensioned side view of the rivet of FIG. 1.

Referring now to FIG. 2A, FIG. 2A is a closer side view of the display rivet 8 of FIG. 1 with nominal dimensions. Each of the plurality of indicated dimensions Y1-Y5 is measured along the central axis A.

The first thickness Y1 of the display plate 18 is preferably in the range of 0.002 inches to 0.015 inches, and more preferably within the range from 0.004 inches to 0.006 inches. The second thickness Y2 of the rivet plate 14 is preferably within the range of 0.015 to 0.035 inches. The third height Y3 of the first cylindrical element 22 is preferably within the range from 0.040 inches to 0.065 inches. The fourth height Y4 of the second cylindrical element 24 is preferably within the range from 0.010 inches to 0.030 inches. The tip height Y5 of the cutting tip 26 is preferably within the range from 0.030 inches to 0.050 inches.

Figure 2B:
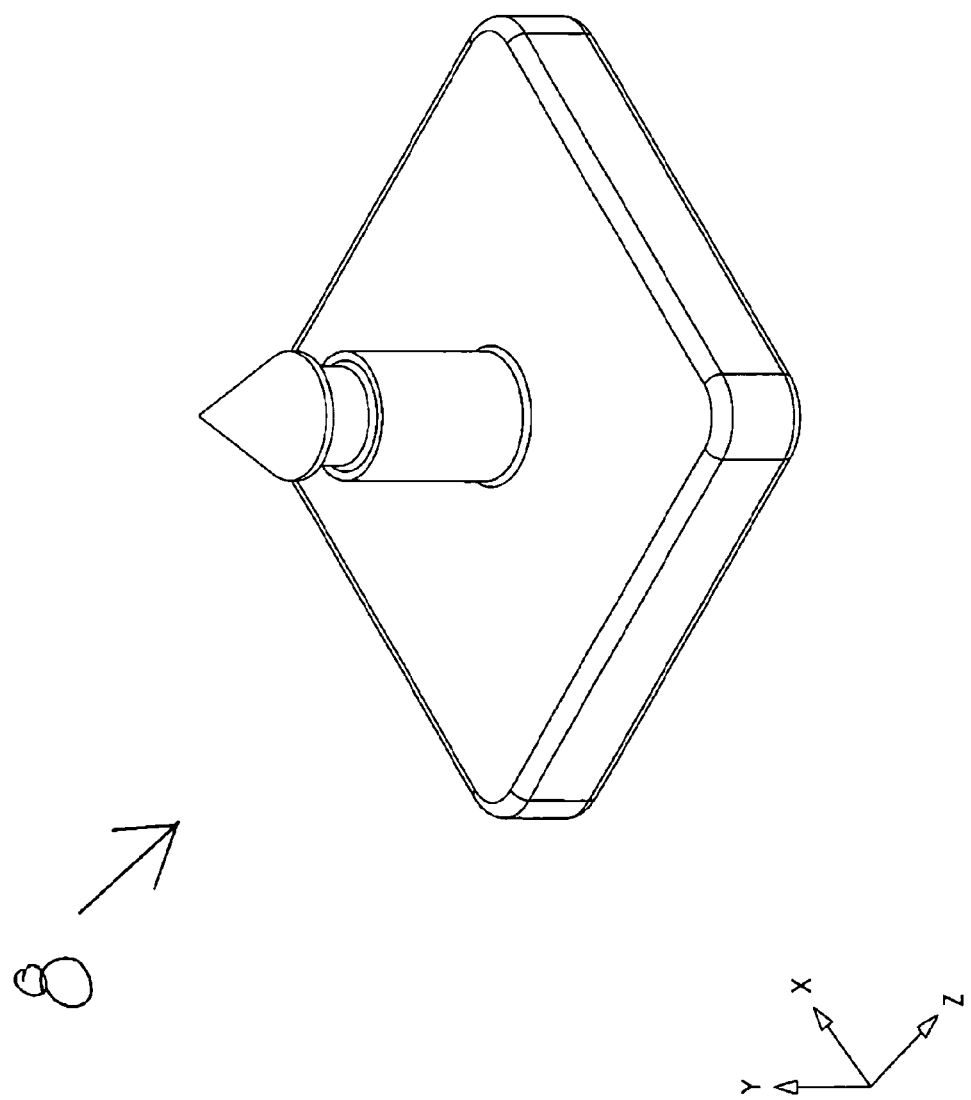
FIG. 2B is a perspective view of the rivet of FIGS. 1 and 2A.

Referring now to FIG. 2B the display rivet 8 of FIGS. 1 and 2A is shown in a perspective view, wherein the rivet post 16 extends along the central axis A that is normal to the display plane D. The central axis A passes directly through a cylindrical center point 54 of the rivet plate 14, and the central axis A is equidistant from each of the four edges of the preferably square display rivet plate 8.

Referring now to FIG. 3, FIG. 3 is a closer side view of the first tag 2 of FIG. 1 and a rodent ear 6 with additional nominal dimensions. The first plurality of indicated dimensions Y6-Y8 are measured along the central axis A, and the second plurality of dimensions X1-X5 are measured at an axis B that is orthogonal to the central axis A. The lower tip diameter X1 of the cutting tip 26 is preferably sized to be from 0.010 inches to 0.020 inches greater than second width X2 of the second diameter 44 of the receiver plate 28. The third diameter X3 of the second cylindrical element 24 of the rivet post 16 is preferably sized to be 0.010 inches to 0.015 inches smaller than both the tip lower diameter X1 and the fourth diameter X4 of first cylindrical element 22. The circular protective channel 36 is preferably sized to have a fifth diameter X5 that is 0.005 inches to 0.400 inches larger than the tip lower diameter X1.

The rodent ear thickness Y6 is likely to be less than 0.035 inches in thickness. In particular examples, a typical mouse ear exhibits a thickness of 0.011 inches and a typical rat ear is about a 0.08 inches thick. The receiver plate thickness Y7 is preferably within the range 0.020 inches to 0.030 inches. The receiver collar height Y8 is preferably in the range of 0.055 inches to 0.075 inches, and a collar wall 56 of the collar 30 has an average thickness orthogonal to the central axis A within the range 0.010 inches to 0.050 inches.

Figure 4:
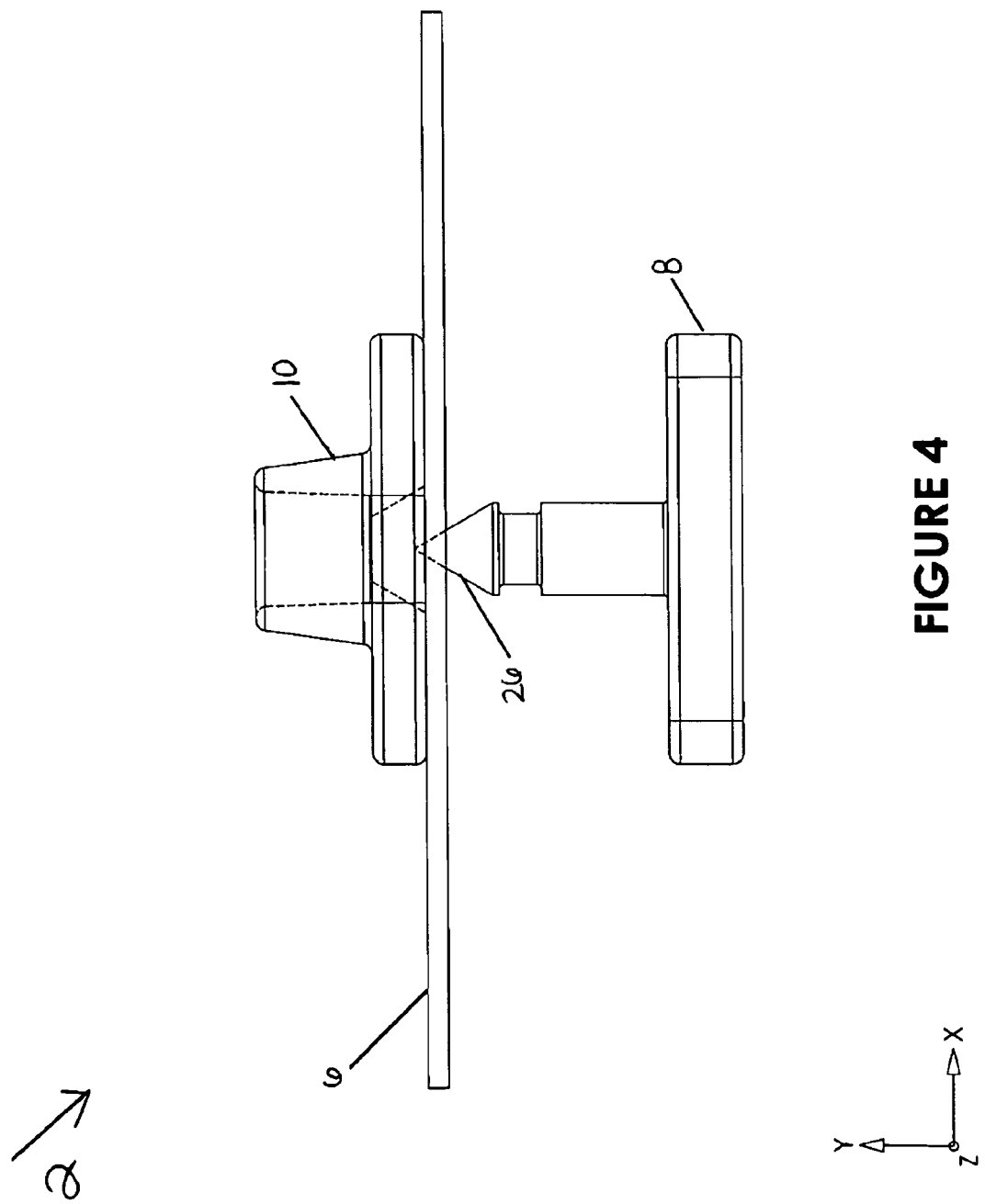
FIG. 4 is a side view of the tag of FIGS. 1 through 3 and wherein a post tip of the first tag has pierced the ear of FIG. 3.

Referring now to FIG. 4, FIG. 4 illustrates the rodent ear 6 having a nominal thickness of 0.010 inches and disposed between the receiver 10 and the rivet 8 of the first tag 2, and wherein the cutting tip 26 of the rivet post 16 is extending through the rodent ear 6.

Referring now to FIG. 5, FIG. 5 illustrates a coupling of the rivet 8 and the receiver 10, wherein the rivet cutting tip 26 is positioned wholly within the protective channel 36 of the receiver collar 30. The cutting tip 26 of the rivet post 16 is impeded from withdrawal through the receiver plate 28 due to the relatively larger diameter of the tip lower diameter 48 in comparison with the narrower second diameter 42 of the angled channel 34 of the receiver plate 28. FIG. 5 further illustrates the first cylindrical element 22 of the rivet post 16 extending through rodent ear 6.

Figure 6:
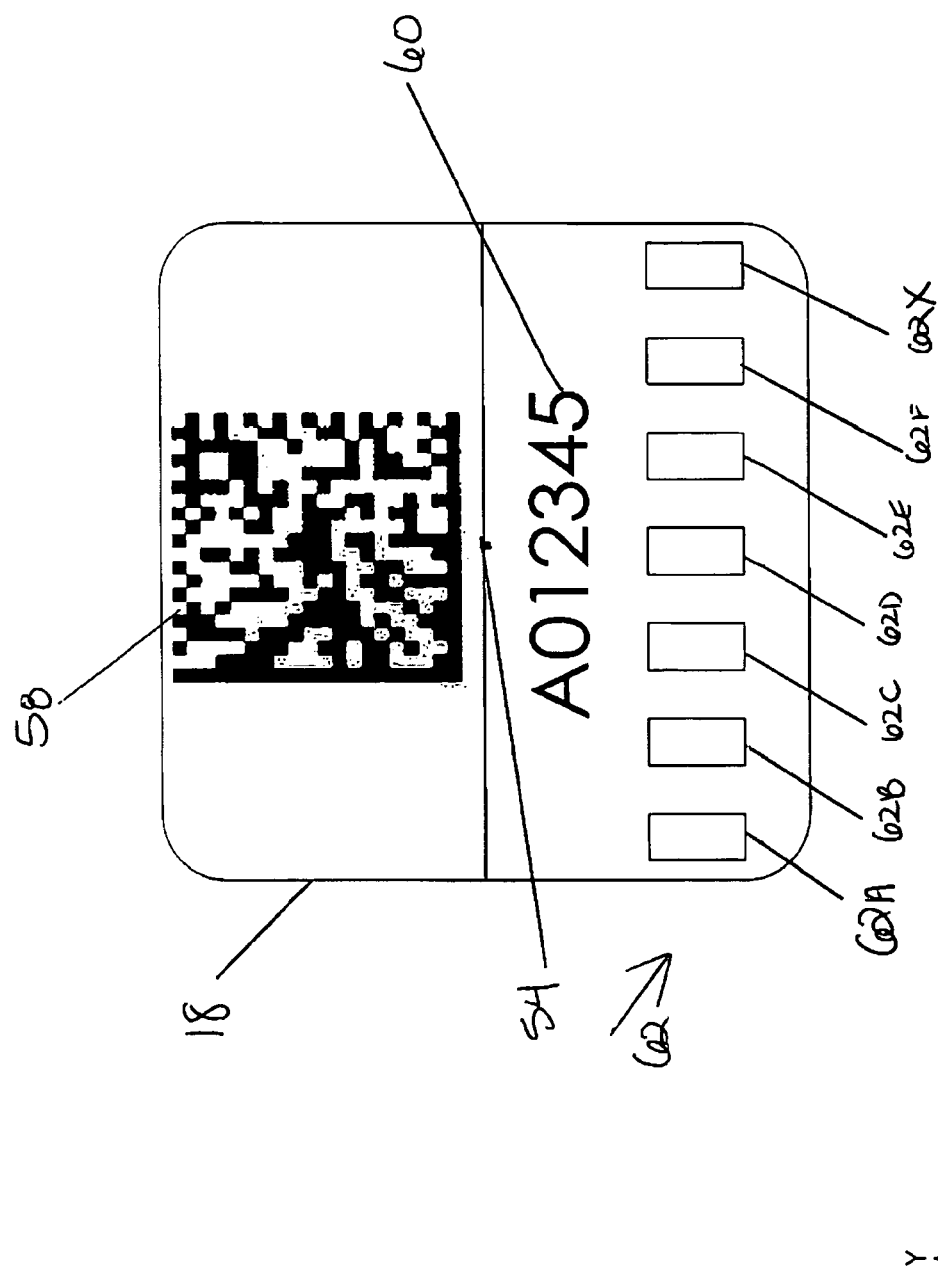
FIG. 6 is a front view of the display plate of the rivet of FIGS. 1 through 5.

Referring now to FIG. 6, FIG. 6 is a front view of the display plate 18 of FIGS. 1 through 5. The display plate 18 may include a bar code pattern 58, an alphanumeric serial numeral 60, and/or a color code pattern 62. The bar code pattern 58 may comprise of a one dimensional bar code image and/or a two-dimensional bar code image. The alphanumeric serial number 60 is preferably printed in point typeset or smaller. The color code pattern 62 includes colored surface areas 62A-62X, wherein each colored surface area 62A-62X is preferably sized at less than ten percent of the surface area of the display plate 18.

The bar code pattern 58, an alphanumeric serial numeral 60, and/or a color code pattern 62 may each comprise a representation of a same serial number in whole or in part. In the exemplary display plate 18, the serial number A012345 may be encoded into the bar code pattern 58 and the printed as or within the alphanumeric serial numeral 60. It is understood that the alphanumeric serial numeral 60 may alternately or additionally use other visual markings, such as squares, ovals, circles, and/or stars that may be color coded.

Alternatively or additionally the color code pattern 62 may be a representation, in whole or in part, of the same serial represented by the alphanumeric serial numeral 60 and/or the alphanumeric serial numeral 60. For example, first colored surface 62A may be a shade of red that indicates a letter A; the second colored surface 62B may be a shade of blue that represents a zero or null values; the third colored surface 62C may be a shade of blue that represents the numeral one; the fourth colored surface 62D may be a shade of yellow that represents the numeral two; the fifth colored surface 62E may be a shade of orange that represents the numeral three; the sixth colored surface 62F may be a shade of green that represents the numeral four; and the seventh colored surface 62F may be a shade of purple that represents the numeral five. It is understood that the color code pattern 62 may alternately or additionally use other color coded areas other than the pictured rectangular shapes, such as squares, ovals, circles, and/or stars.

Referring now to FIG. 7, FIG. 7 illustrates an exemplary mouse 4 as the host animal 4 of the first tag 2, wherein the first tag 2 is attached to the previously presented exemplary rodent ear 6. The mouse 4 is shown within a three-dimensional cage 64 having a cage card 66 affixed to a cage wall 68. The cage card 66 may be an Oxford Ruled Index Card™ cardboard stock card product code 0 78787 03104 distributed by Esselte, Inc. of Melville, N.Y.

The cage is configured to at least temporarily hold or house the mouse 4. The cage card 64 includes one or more aspects of the image of the display plate of FIG. 6, such as the same bar code pattern 58, the same alphanumeric serial numeral 60, and/or the color code pattern 62, or optionally an image that is derived from, or selected from, an aspect of the image of FIG. 6. The mouse 4 may wear the first tag 2 during a course of study or observation and for the remainder of its life.

Figure 8A:
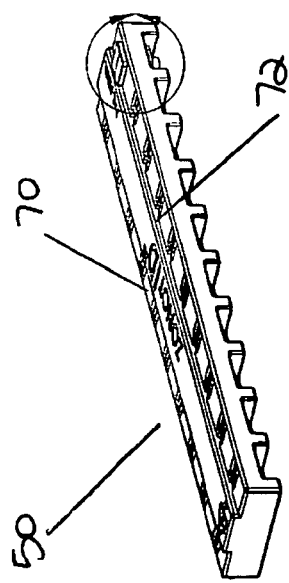
FIGS. 8A-8C are representations of a tray configured to hold and protect the tag of FIGS. 1 through 7.
Figure 8C:
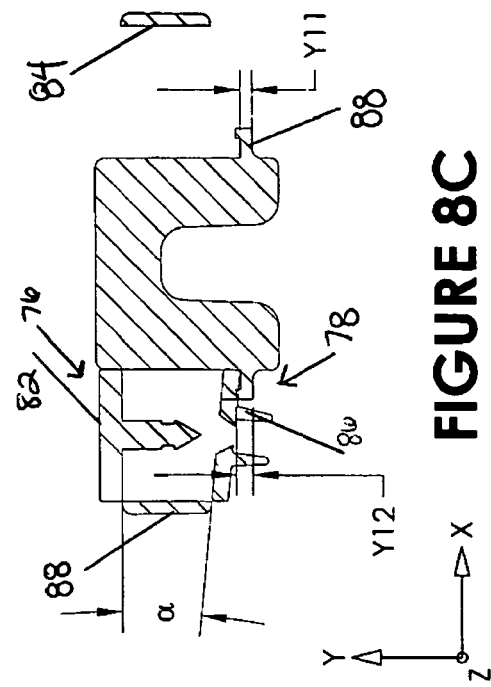
Figure 8B:
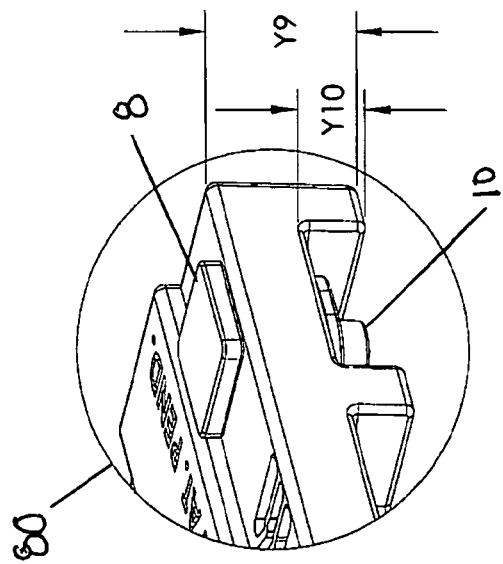

Referring now to FIGS. 8A through 8C, three views of the exemplary tray 50 configured to hold and protect a plurality of first tags 2 are presented. FIG. 8A is a perspective view of the exemplary tray 50 configured to hold a plurality of ten first tags 2 on each of two sides 70 & 72. Each of a plurality of twenty tag sites 74 of the tray 50 includes a rivet segment 76 for holding and protecting the rivet 8 and a receiver segment 78 for holding and protecting the receiver 10. The tray 50 additionally positions the rivet 8 and the receiver 10 for withdrawal from the installation in a tag site 74 by means of the applicator 52. The tray 50 comprises polypropylene, or other suitable thermoplastic known in the art that may or may not withstand a standard medical autoclave process and allows for an interference fit with the tag rivet 8 and the tag receiver 10. The tray 50 may optionally further comprise a dye material or colored substance that causes the tray 50 to present one or more colors visible to the human eye, such as red, blue, yellow, orange, green, purple.

FIG. 8B is a detailed perspective view of an exemplary right corner tag site 80 of the tray of FIG. 8A. The ninth height Y9 of the exemplary tray site 80 is preferably on the order 0.280 inches plus or minus 0.002 inches, and a receiver aperture capture height Y10 of the exemplary tag site 80 is preferably 0.002 inches greater than the total height of the receiver 10, i.e. the sum of the heights Y7 and Y8 as designated in FIG. 3, in order for the exemplary receiver segment 78 to substantially enclose and protect a receiver installed therein.

FIG. 8C is a side cut away view of a second exemplary tag site 82 and a third exemplary tag site 84, wherein an exemplary second tag site 82 is illustrated with an installed tag rivet 8 and tag receiver 10. An exemplary first receiver ledge 86 and a first wall 88 are positioned and configured to maintain the tag receiver 10 at an approach angle alpha, whereby the approach angle alpha is preferably in the range 3 degrees to 8 degrees. Maintenance of the tag receiver 10 at the approach angle alpha enables a smoother engagement of the receiver 10 with the applicator 52 when the applicator 52 is applied to remove the tag receiver 10 from second exemplary tag site 82. An eleventh vertical thickness Y11 of a second receiver ledge 9-0 and a twelfth vertical thickness 12 of the first receiver ledge 86 are preferably on the order of 0.025 inches plus or minus 0.002 inches. The first wall 88 and the first receiver ledge 86 are positioned to enable an interference fit preferably on the order 0.002 inches with the tag receiver 10 as installed within the receiver segment 78 of the exemplary tag site 82. For example, when the receiver plate 28 has a cross sectional planar area of 0.200 inches by 0.200 inches, a pre-insertion distance, i.e., a distance evidenced when the receiver segment 78 is empty and not containing the tag receiver 10, between the first wall 88 and the first receiver ledge 86 is preferably 0.198 inches along a line extending from the first wall 88 and toward the first receiver ledge 86 at the application angle alpha.

Figure 9:
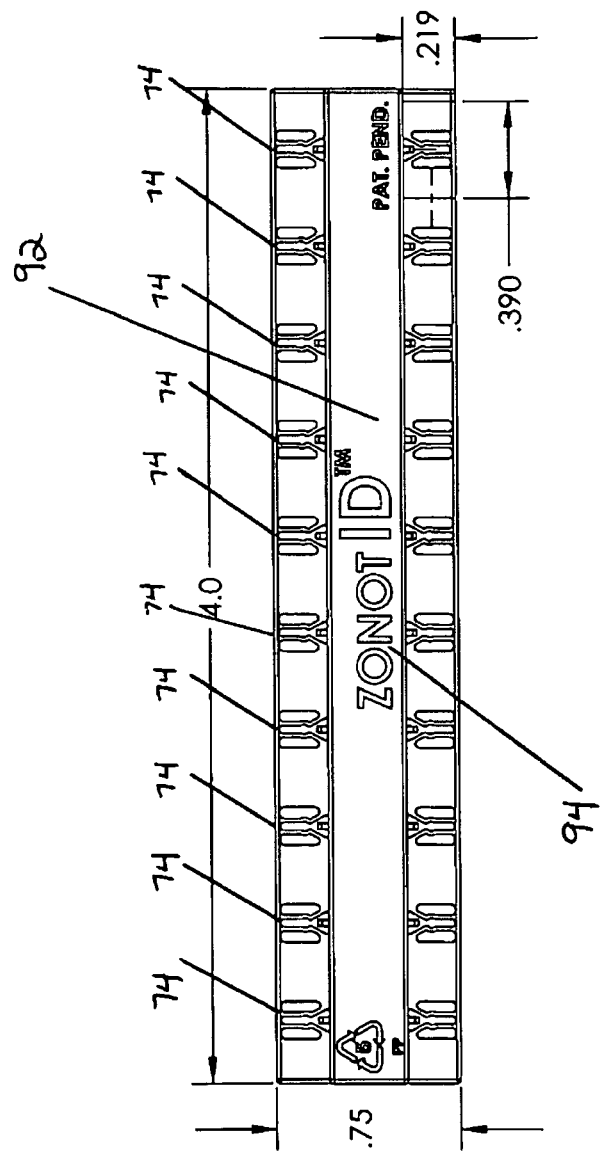
FIG. 9 is a top view of the tray of FIGS. 8A, 8B and 8C.

FIG. 9 is a top view of the exemplary tray 50 of FIGS. 8A-8C. The tray 50 has a width of 4.0 inches and a depth of 0.75 inches. The exemplary first corner tag site 80 presents a width of 0.390 inches and a depth of 0.219 inches. A center strip 92 of the tray 50 provides stability to the plurality of tray tag sites 74 and enables the inclusion of corporate signage 94 and product related information.

Figure 10:
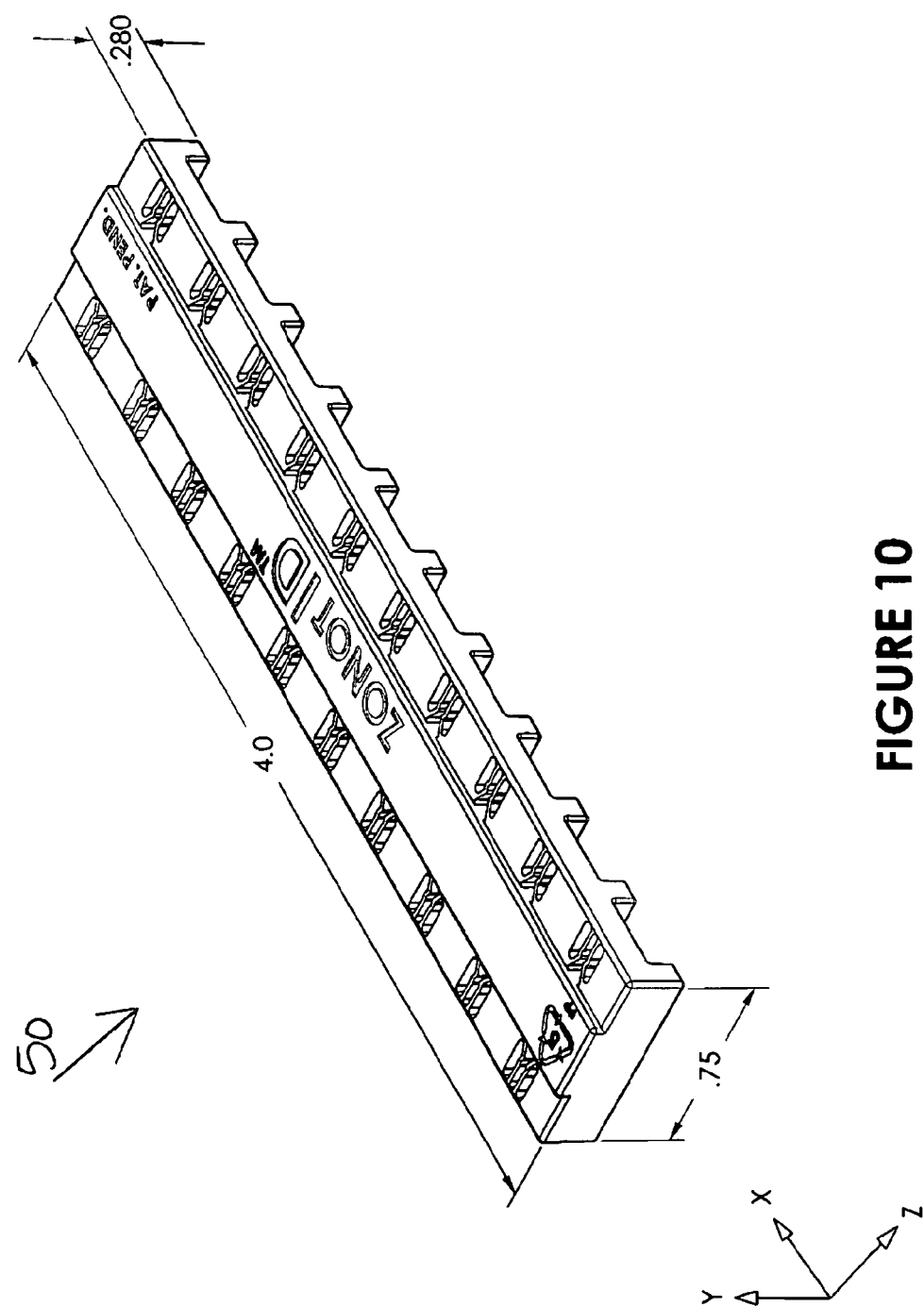
FIG. 10 is a perspective view of the tray of FIGS. 8A, 8B, 8C and 9.

FIG. 10 is a perspective view of the tray 50 of FIGS. 8 and 9, wherein the height of the exemplary first corner tray site is shown to be 0.280 inches, and the tray width of 4.0 inches and depth of 0.75 inches are indicated.

Figure 11:
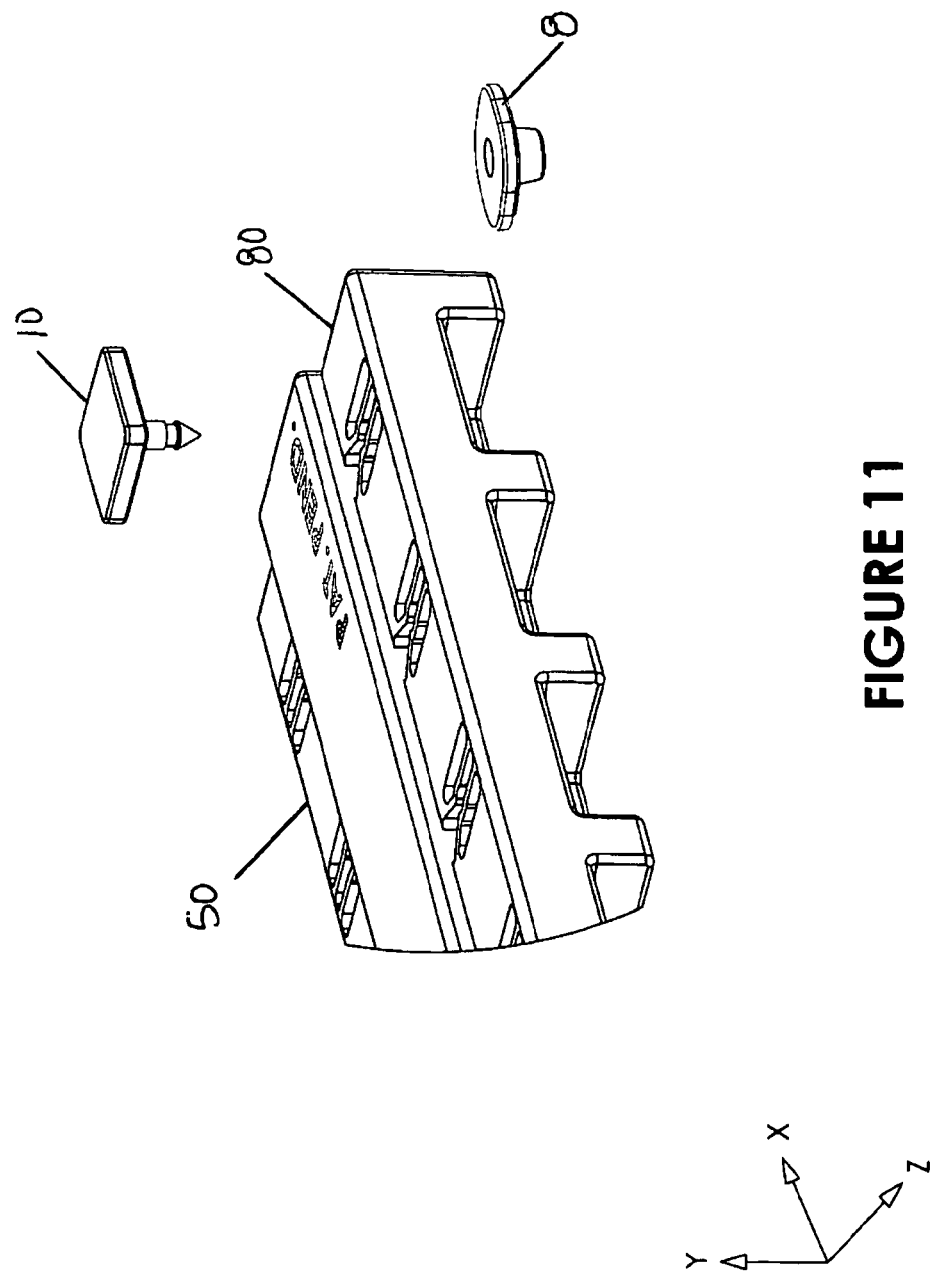
FIG. 11 is a partial, detailed perspective view of the tray of FIGS. 8A through 10.

FIG. 11 is a detailed perspective view of the exemplary first right corner tag site 80 shown in relationship to the tag rivet 8 and the tag receiver 10 but prior to installation of the tag 2 at the first corner tag site 80.

Figure 12:
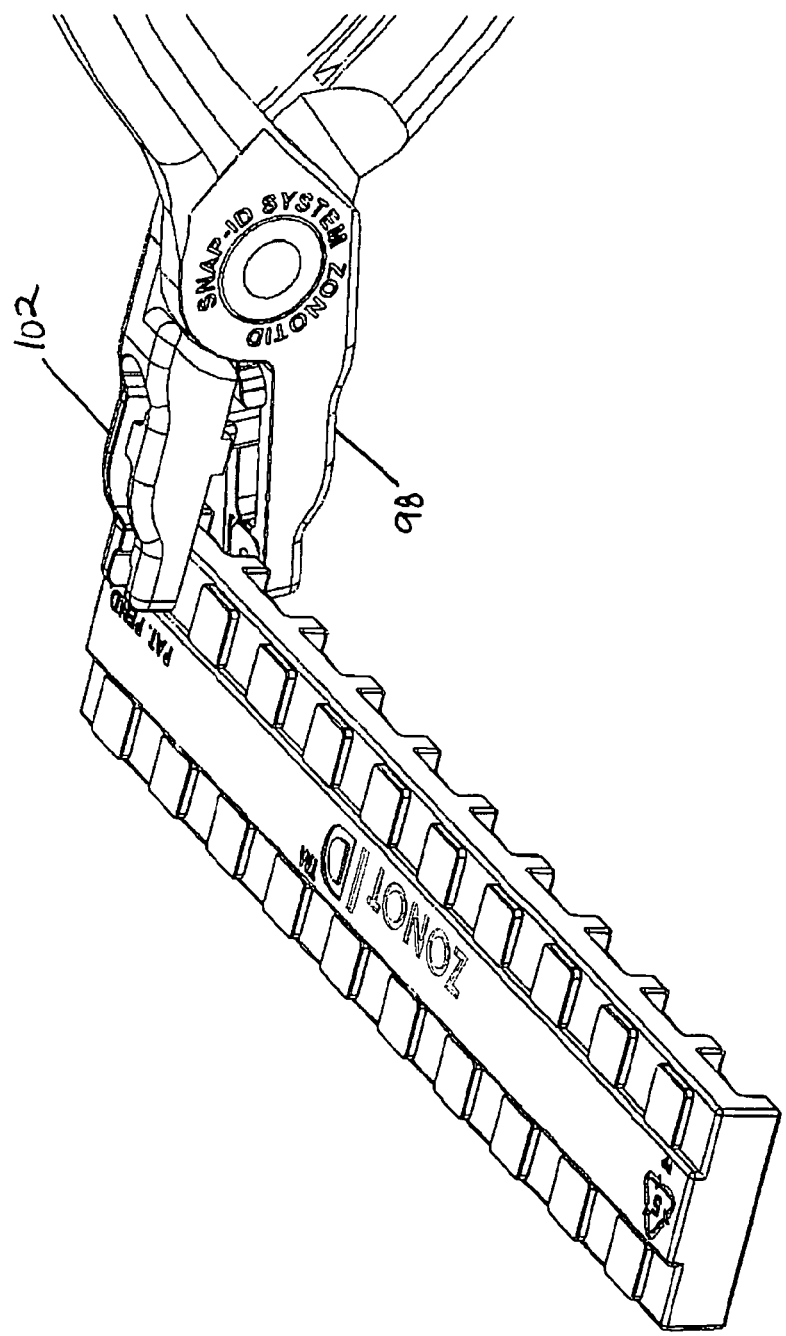
FIG. 12 is a partial perspective view of an applicator positioned over a tag site of the tray of FIGS. 8A through 11.

FIG. 12 is a perspective view of the tray of FIGS. 8A-8C and 9 through 11 wherein a plurality of twenty tags 2 are each installed at separate tag sites 74, and the applicator 52 is positioned proximate to the tag 2 installed at the first corner tag site 80. The applicator 52 as positioned in FIG. 12 has both (1.) engaged with and removed the tag receiver 10 from the receiver segment 78 of the first corner tag site 80; and (2.) engaged with and removed the tag rivet 8 from the rivet segment 76 of the first corner tag site 80.

As mentioned previously, it is understood that it is preferable that the receiver plate 28 and the rivet plate 14 present a square shape in order allow the easier engagement of the tag 2 with both the tray 50 and the applicator 52.

Figure 13:
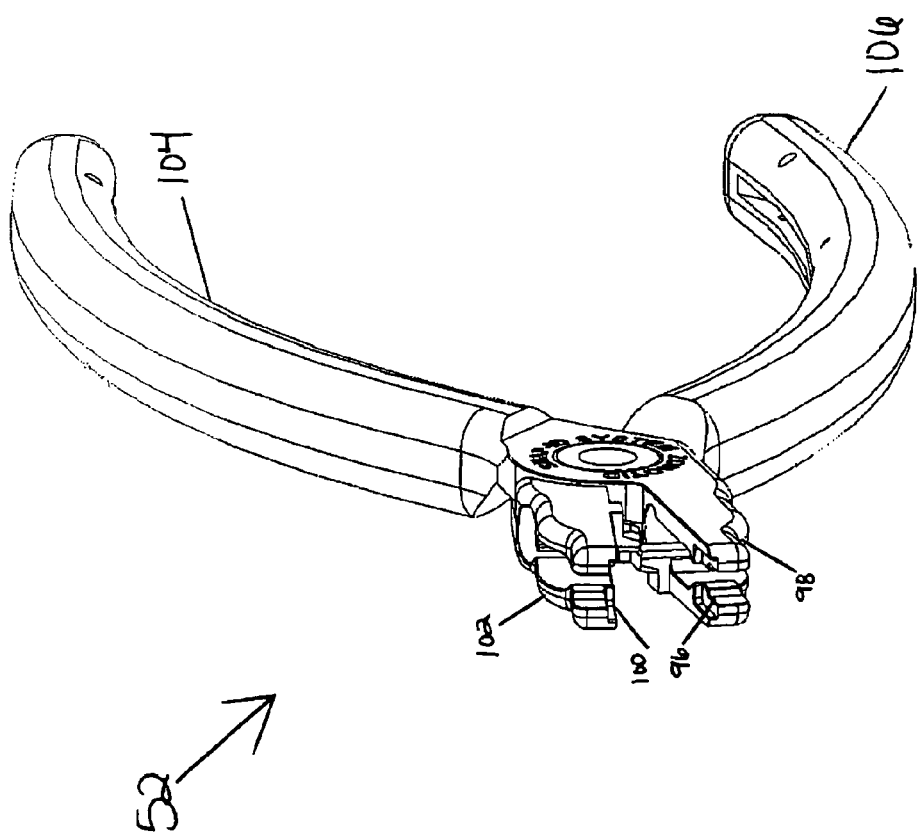
FIG. 13 is a perspective view of the applicator of FIG. 12.

FIG. 13 is a perspective view of the applicator 52. An orthogonal lower recess 96, or receiver recess 96, of a receiver jaw 98 is sized to enable an interference fit with the tag receiver 10 wherein the receiver recess 96 has an aperture approximately 0.005 inches smaller in width than each of the two cross-sectional dimensions of the receiver plate 28. For example, when the receiver plate 28 has a cross-sectional area 0.200 inches by 0.200 inches, the receiver recess 96 preferably has a width of 0.195 inches and a depth on the order of 0.200 inches.

An orthogonal upper recess 100, or rivet recess 100, of a rivet jaw 102 is sized to enable an interference fit with the tag rivet 8 wherein the rivet recess 100 has an aperture approximately 0.005 inches smaller in width than each of the two cross-sectional dimensions of the rivet plate 14. For example, when the rivet plate 14 has a cross-sectional area 0.200 inches by 0.200 inches, the rivet recess 100 preferably has a width of 0.195 inches and a depth on the order of 0.200 inches.

The applicator jaws 98 & 102 are preferably made of a material more rigid than the tray 50 to enable the interference fits of the tag rivets 8 and tag receivers 10 respectively enable a user to apply manual force to overcome the force applied by the tray 50 and holding the rivets 8 and the receivers 10 in the tray 50. For example, when the tray 50 is made substantially of a deformable plastic such as polypropylene, the rivet jaw 102 and the receiver jaw 98 may be or comprise steel, stainless steel, or aluminum, or other suitable material known in the art that is more rigid and less deformable than the tray 50 at normal ambient temperatures of a laboratory, such as within temperatures in the range from 65 degrees Fahrenheit to 75 degrees Fahrenheit.

Figure 14:
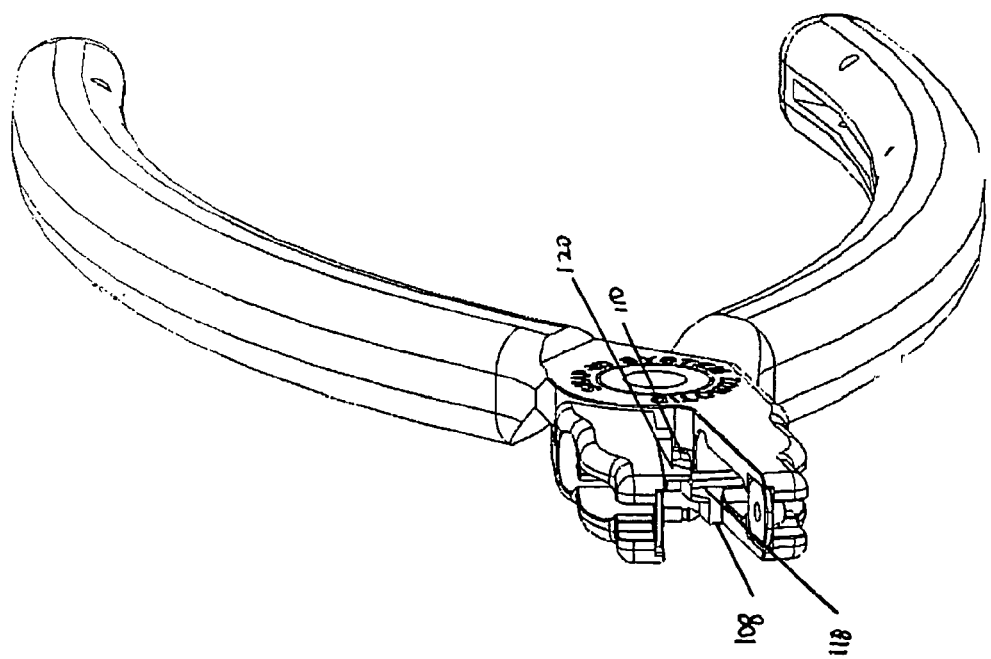
FIG. 14 is a perspective view of the applicator of FIGS. 12 and 13, wherein the receiver and rivet of FIGS. 1 through 8C are separately held by the applicator.

FIG. 14 is a perspective view of the applicator 52 of FIGS. 12 and 13 and wherein the tag rivet 8 is held by an interference fit in the rivet recess 100 and the tag receiver 10 is held by an interference fit in the receiver recess 96.

Figure 15:
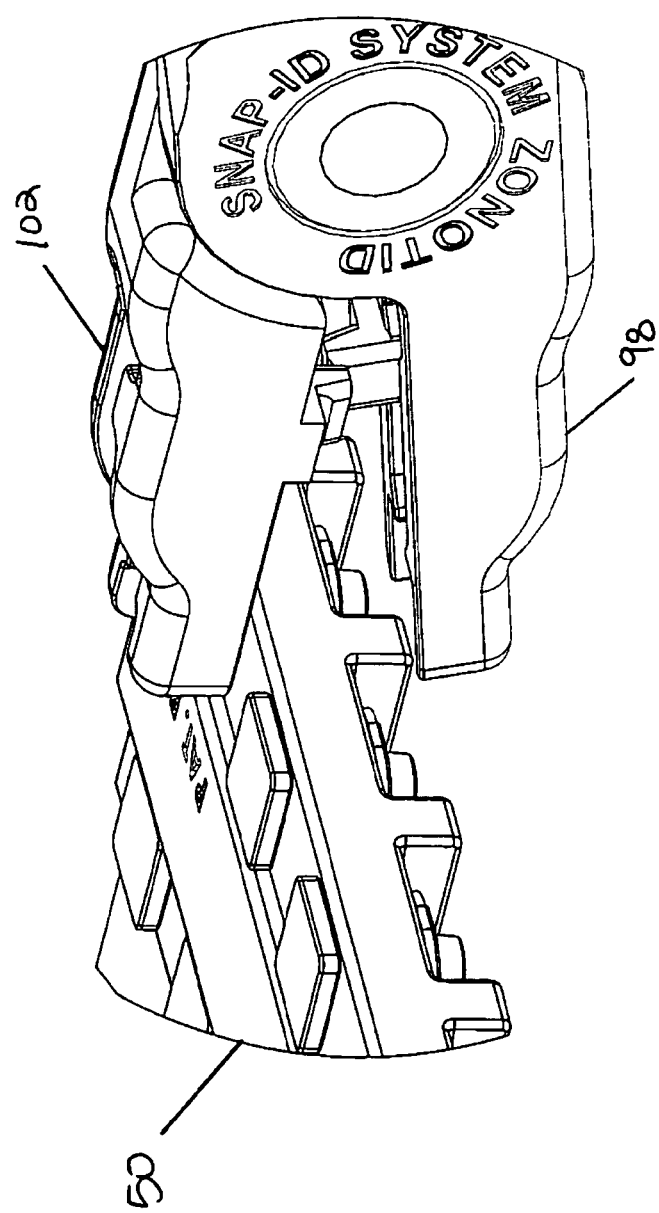
FIG. 15 is a partial perspective view of the applicator of FIGS. 12-14 positioned proximate to the tray of FIGS. 8A through 12.

FIG. 15 illustrates the upper rivet jaw 102 and the lower receiver jaw 98 proximate to and partially positioned onto and below an individual tag 2 as installed in the first corner tag site 80. The applicator 52 and tray 50 are configured to enable the jaws 98 & 102 to engage with the tag 2 as installed at a tag site 74 without damaging or permanently deforming the tray 50.

Figure 16:
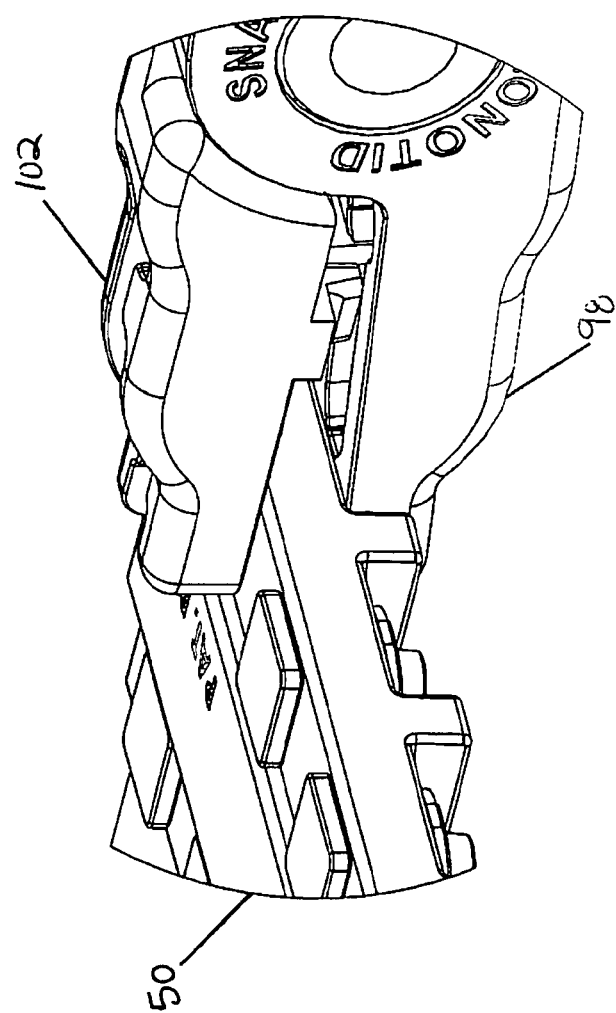
FIG. 16 is a partial perspective view of the applicator of FIGS. 12-15 coupled with the receiver and rivet of FIGS. 1 through 8, wherein the receiver and tray are simultaneously installed within the tray of FIGS. 8A through 12, and 15.

FIG. 16 presents the applicator 52 having achieved an interference fit between both (1.) the rivet 8 and the rivet recess 100 of the rivet jaw 102; and (2.) the receiver 10 and the receiver recess 96 of the receiver jaw 98. It is understood that the interference fits of both the receiver recess 96 and the receiver 10 and the rivet recess 100 and the rivet 8 are achieved prior to removal of the receiver 10 and the rivet 8 from the tag site 74.

Figure 17:
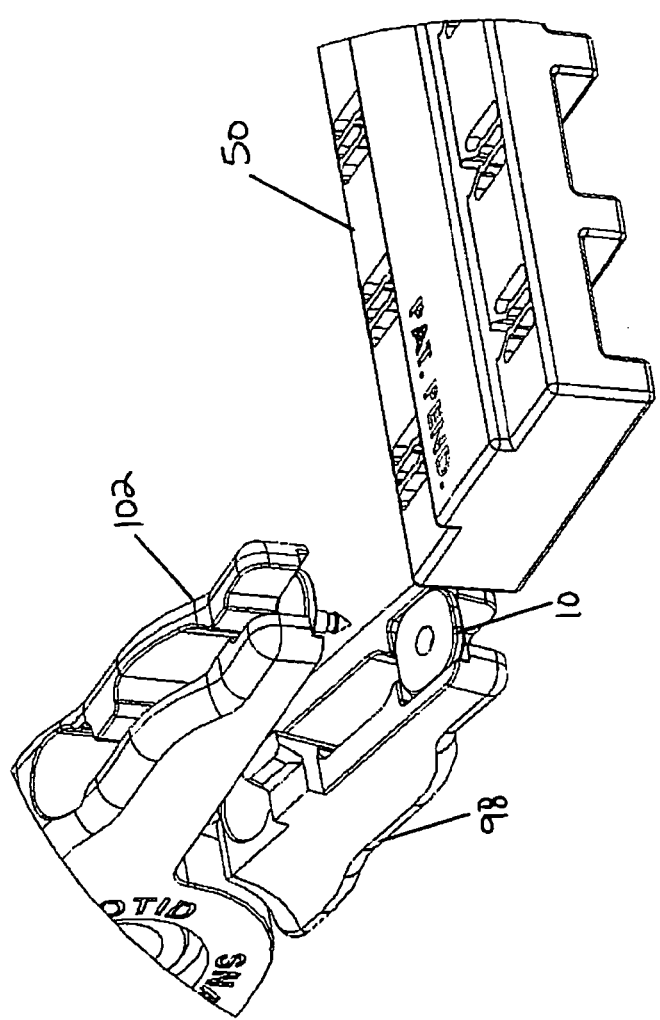
FIG. 17 is a partial perspective view of the applicator of FIGS. 12 through 16 engaged with the receiver and rivet of FIGS. 1 through 8, and FIGS. 11, 12, 14, 15 and 16 after the applicator has removed the receiver and rivet from the tray of FIGS. 8A through 12, 15 and 16.

FIG. 17 illustrates the applicator 52 at a position of withdrawal away from the tray 50 and after the rivet 8 and the receiver 10 have been pulled out of the hosting tray site 74. It is understood that the positions of the receiver jaw 98 and the rivet jaw 102 of FIGS. 13 through 20 are achieved by manipulation of a combination of each of a pair of handles 104 & 106 of the applicator 52.

Figure 18:
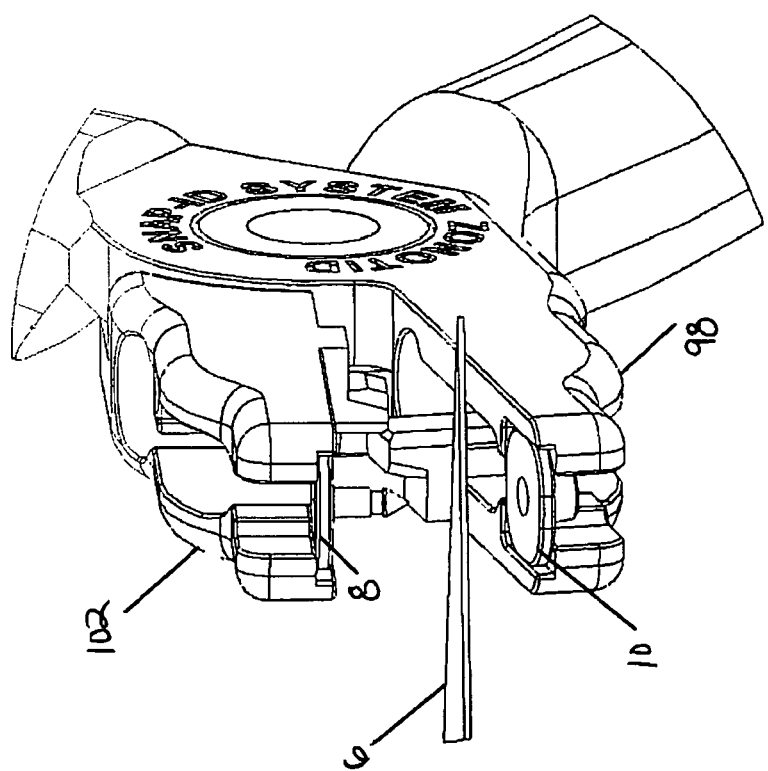
FIG. 18 is a partial perspective view of the applicator of FIGS. 12 through 17 holding a rivet and receiver of FIGS. 1 through 8, 11, 12, and 14 through 17 respectively on either side of a target rodent ear of FIGS. 4 through 5.

FIG. 18 illustrates the rivet 8 and the receiver 10 positioned respectively on either side of the rodent ear 6 of FIGS. 3, 4 and 5. The applicator 52 may be placed in the orientation as shown relative to the rodent ear 6 of FIG. 18 by manual positioning accomplished by the user's grasp of the handles 104 & 106.

Figure 19:
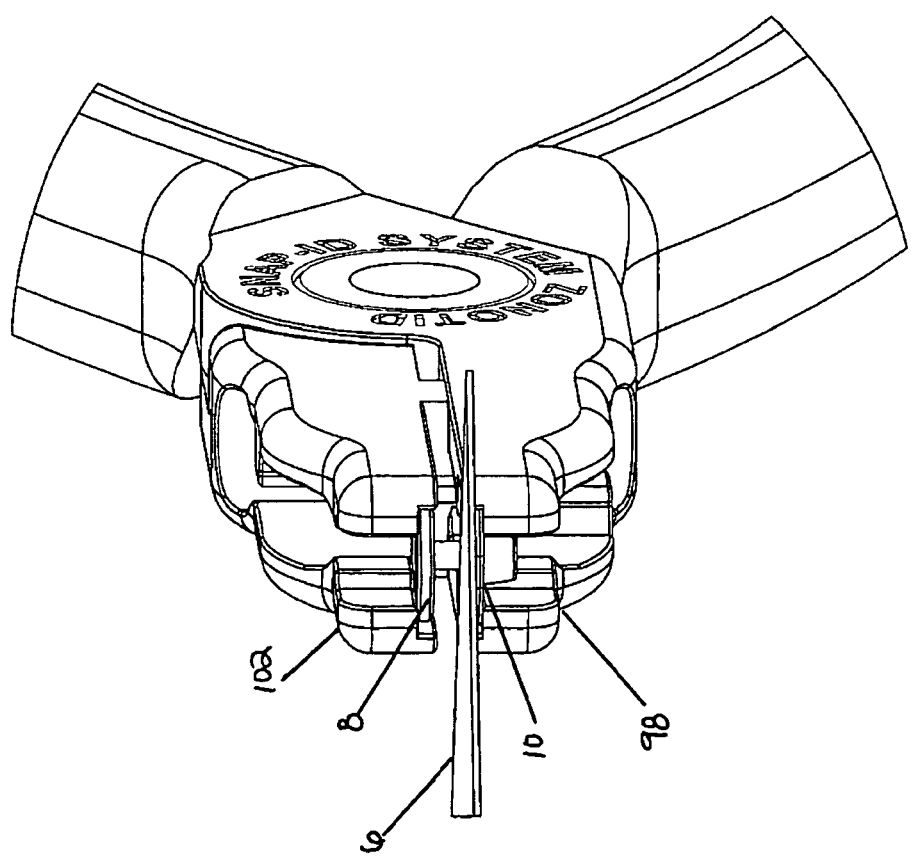
FIG. 19 is a partial perspective view of the applicator of FIGS. 12 through 18 holding a rivet and receiver of FIGS. 1 through 8, 11, and 14 through 18 piercing the target rodent ear of FIGS. 4 through 5.

FIG. 19 illustrates the applicator 52 in a second position wherein the cutting tip of the rivet post 16 has been forced wholly through the ear 6 and receiver plate 28 and resides within the protective channel 36 as formed by the receiver collar 30. The rivet post 16 is thus extending through the rodent ear 6 and the tag 2 is coupled to the rodent ear 6 by the impedance of withdrawal of the tip 26 through the angled channel 34 imposed by the narrower second diameter 42 of the second side 44 of the receiver plate 28. The second position of the applicator 52 is achieved by the user grasping the applicator handles 104 & 106 and manually applying force to drive the handles 104 & 106 together.

Figure 20:
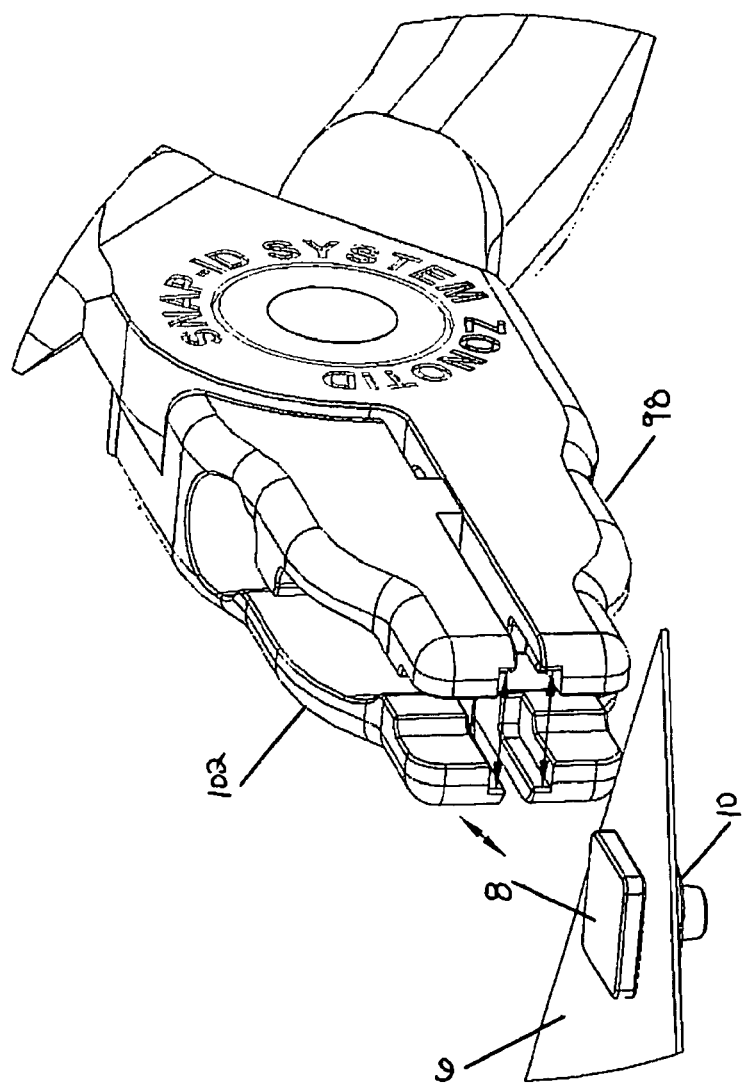
FIG. 20 is a partial perspective view of the applicator of FIGS. 12 through 19 after coupling a rivet and receiver of FIGS. 1 through 8, 11, 12, and 14 through 19 to the target rodent ear of FIGS. 4 through 5.

FIG. 20 illustrates the applicator 52 in a third position, wherein the first tag 2 is released from coupling with the applicator 52. The third position is achieved by the user applying additional force in squeezing the applicator handles 104 & 106 together beyond that force required to achieve the second position. As force is applied by the user to drive the handles 104 & 106 together and closer than required for the second position, the receiver jaw 98 and the rivet jaw 102 are splayed apart along an X-axis that is orthogonal to the both the length of the handles 104 & 106 and the central axis A of the rivet. A pair of raised stops 108 & 110 located respectively on the receiver jaw 98 and rivet jaw 102 limit the closing travel of the receiver jaw 98 and the rivet jaw 102 of the applicator 52 so that the rivet 8 and the receiver 10 cannot over engage and potentially damage the rodent ear 6 or the first tag 2 itself.

For example and not recited in limitation, the stops 108 & 110 may limit the receiver jaw 98 and rivet jaw 102 from forcing the rivet plate 14 be forced closer than 0.060 inch to the receiver 10 along the axis A. This movement limitation of the jaws 108 & no caused by the stops 108 & no thereby prevents the user from applying a force to the applicator 52 that causes the jaws 98 & 102 to the crush the rivet post 16 against receiver 10. More particularly, the limitation of the travel of the jaws 98 & 102 along the axis A imposed by the stops 108 & no may reduce an incidence of damage caused to first tags 2 during attachment to animal ears 6.

Figure 21:
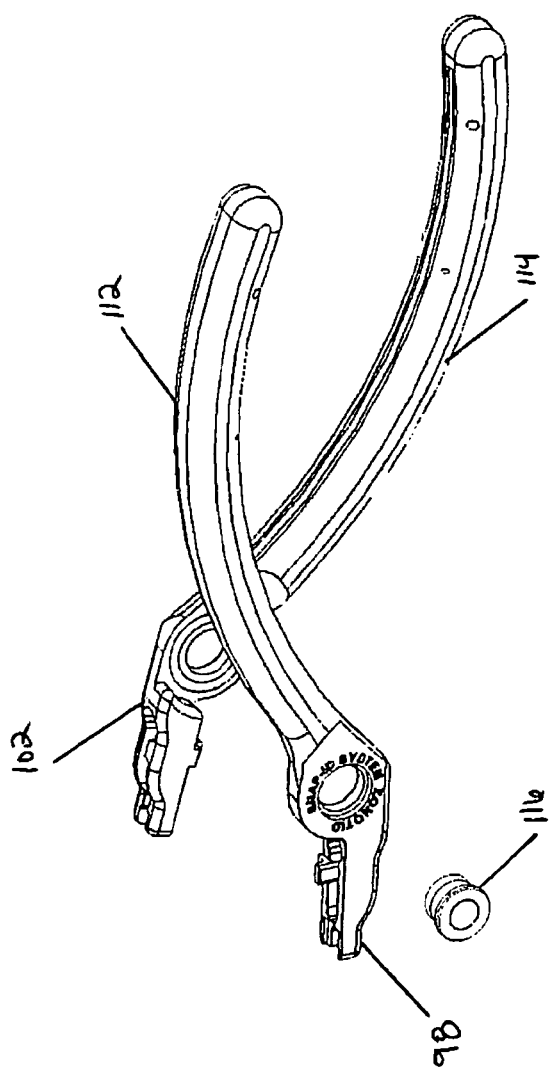
FIG. 21 is an exploded view of the applicator of FIGS. 12 through 20.

FIG. 21 is an exploded view of the three components of the applicator 52. The first piece 112 includes a first handle 104 and the receiver jaw 98. The second piece 114 includes a second handle 106 and the rivet jaw 102. The first piece 112 and the second piece 114 are rotatably coupled by a pivot pin 116. Each handle 104 & 106 are preferably from one to six inches in length extending away from the pivot pin 116 and the jaws 98 & 102.

The receiver jaw 98 includes a lower angled post 118 that includes the lower raised stop 108. The rivet jaw 102 includes an upper angled post 120 that includes the upper raised stop no. The lower angled post 118 is sized and positioned to engage with the rivet jaw 102 when the applicator achieves the second position, and as the applicator 52 is driven into the third position the lower angled post 118 delivers a displacing force to the rivet jaw 102. The upper angled post 120 is sized and positioned to engage with the receiver jaw 98 when the applicator 52 achieves the second position, and as the applicator 52 is driven into the third position the upper angled post 120 delivers a laterally displacing force to the receiver jaw 98. The simultaneous delivery of displacing forces by the upper angled post 120 and the lower angled post 118 causes the receiver jaw 98 to splay laterally and thereby cause the width of the receiver recess 96 to increase. The interference fit of the receiver 10 into the receiver recess 96 is thus terminated as the width of the receiver recess 96 is extended beyond the cross-sectional side length of the receiver plate 28, and the receiver 10 is thus no longer coupled with the receiver jaw 98 when the applicator 52 is in the third position.

The simultaneous delivery of laterally displacing forces by the upper angled post 120 and the lower angled post 118 further causes the rivet jaw 102 to splay laterally and thereby cause the width of the rivet recess 100 to increase. The interference fit of the rivet 8 into the rivet recess 100 is thus terminated as the width of the rivet recess 100 is extended beyond the cross-sectional side length of the rivet plate 14, and the rivet 8 is no longer coupled with the rivet jaw 102 when the applicator 52 is in the third position.

The user may thus remove the tag 2 from the tray 50 by manually driving the handles 104 & 106 together and creating interference fits with the rivet 8 and the receiver 19 that are more forceful than the separate holding forces that the tray 50 applies respectively to the rivet 8 and to the receiver 10. In addition, the user may couple the tag 2 to the rodent ear 6 by pressing the handles 104 & 106 together and causing the cutting tip 26 of the rivet 8 to drive fully through the ear 6 and then fully through the angled channel 34 of the receiver 10. The user may then drive the handles 104 & 106 closer together than the second position requires, and terminate the interference fit of the receiver 10 with the receiver jaw 98 and the rivet 8 with the rivet jaw 102, whereby the applicator 52 has a two phase range of motion. The first phase is instantiated by the user manually forcing the applicator 52 into the second position, and the second phase is instantiated by the user manually forcing the handles 104 & 106 closer together and from the second position and into the third position.

Figure 22:
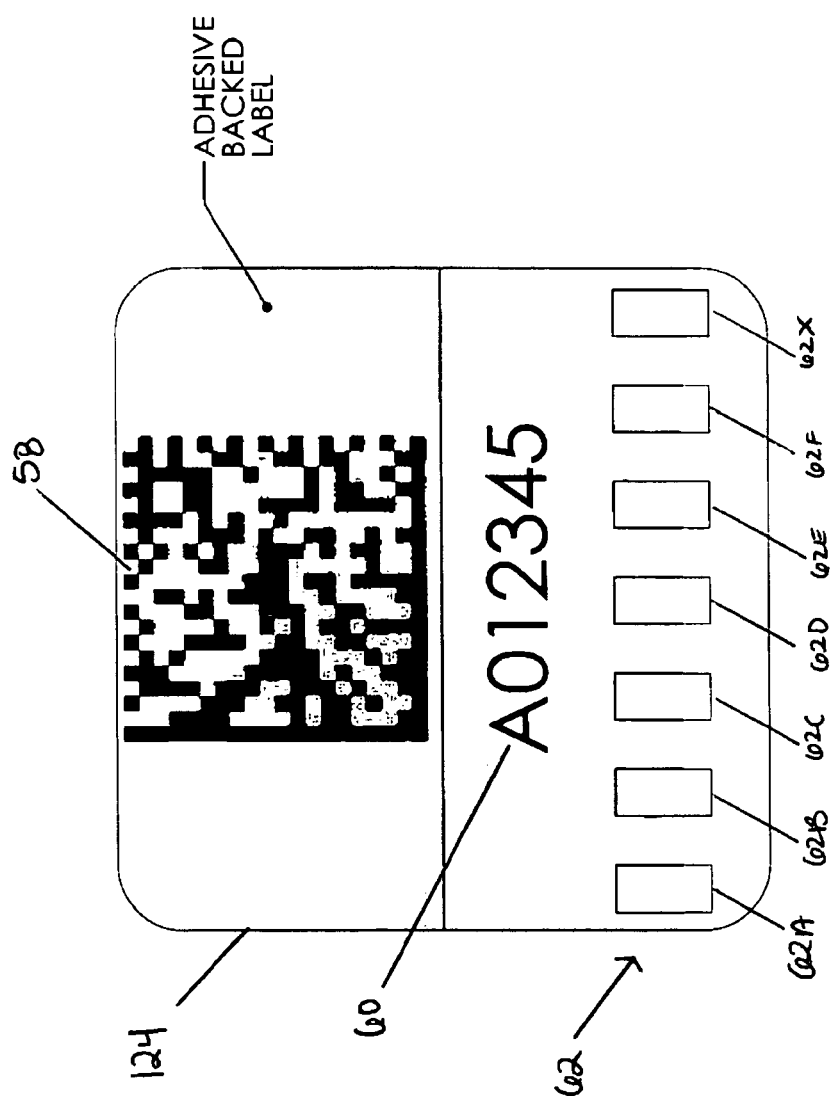
FIG. 22 is a an adhesive backed label bearing the images identical to, or derived from, in whole or in part, the images of the display plate of FIG. 6.

Referring now to FIG. 22, FIG. 22 is a front view of a sticker 122. The sticker 122 may include a sticker adhesive 124 backing that enables the sticker 122 to be affixed to the cage 64 or sample receptacle, e.g. a test tube, and or coupled with an object or a bar code 58 to be visually observed. The sticker 122 is sized to enable the user to confirm that the tag 2 affixed to the rodent 4 resident of the cage 64 is matched with, or alternately associable with but not matched with, the information coded and visually displayed by the sticker 122 and/or the cage card 66. The intended visual correlation between the tag 2 and the cage card 66 thereby enhances the accuracy and ease of performing an animal census of a plurality of animals 4 or a plurality of organic samples derived from animals 4 within a laboratory, experimental facility, or other animal management operation.

The sticker 122 is sized to enable the user to confirm that the tag 2 affixed to the rodent 4 resident of the cage 64 is matched with, or not matched with, the information coded and visually displayed by the sticker 122 on a sample receptacle (test tube) and or coupled with an object or a bar code 58 to be visually observed. The sticker 122 is sized to enable the user to confirm that the tag 2 affixed to the rodent resident 4 of the cage 64 is matched with, or not matched with, the information coded and visually displayed by the sticker 122 on a sample receptacle. The intended visual correlation between the tag 2 and the sample receptacle thereby enhances the accuracy and ease of performing sample processing and or analyses of samples derived from a plurality of animals 4 within a laboratory, experimental facility, or other animal management operation.

The sticker 122 may be a Multi Use Label™ white backgrounded, removable labeling sticker part number 05453 marketed by Avery Dennison Corporation of Brea, Calif.

Referring now to FIGS. 23A and 23B, FIG. 23A is a front view of the applicator 52 engaging with the tray 50 wherein the tag rivet 8 is interference fit into the rivet recess 100 of rivet jaw 102 while the tag rivet 8 still held by the right corner tag site 8. The tag receiver 10 as shown in FIGS. 23A and 23B is not engaged with the receiver recess 96 of the receiver jaw 98. FIG. 23B is a perspective view of the applicator 52 approaching the tray 50 but not touching the first tag 2.

Figure 24B:
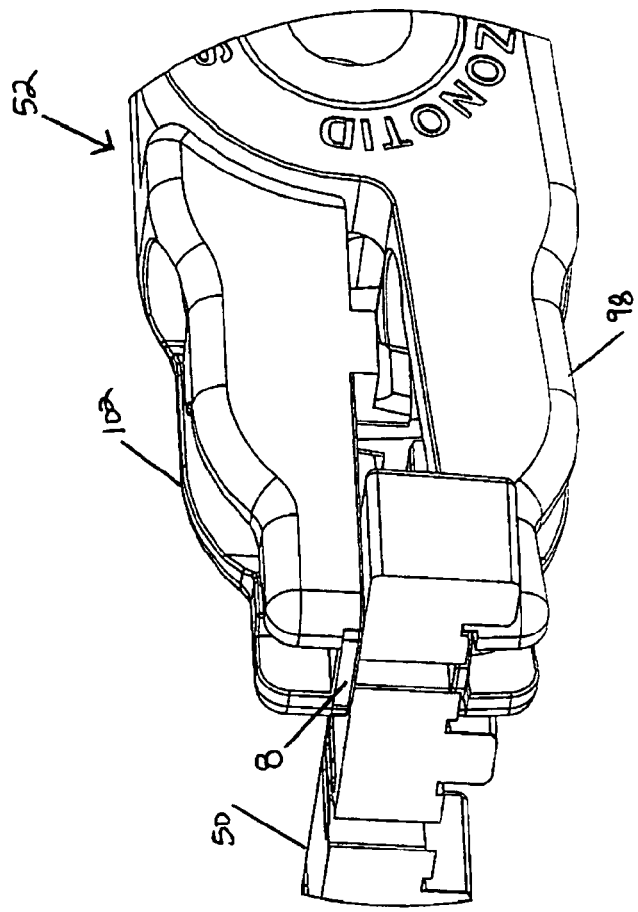
FIG. 24B is a perspective view of the applicator of FIGS. 12 through 21, 23B, and 24A engaged with both the tag rivet of FIGS. 1 through 8, 11, 12, 14 through 20, 23A, 23B and 24A and the tag receiver of FIGS. 1, 7, 8, 11, 12, 14 through 20, 23A 23B and 23A while the tag rivet and the tag receiver are held by the tray of FIGS. 8A through 12, 15 through 17 and 23.
Figure 24A:
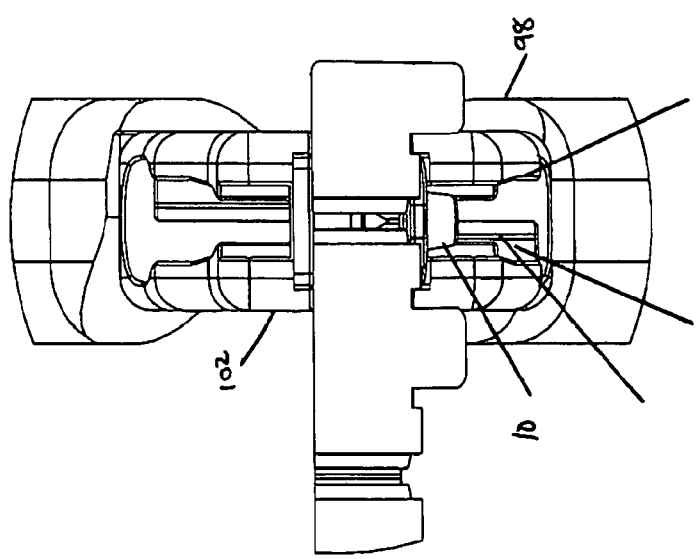
FIG. 24A is a front view of the applicator of FIGS. 12 through 21 and FIG. 23B engaged with both the tag rivet of FIGS. 1 through 8, 11, 12, 14 through 20, 23A and 23B and the tag receiver of FIGS. 1, 7, 8, 11, 12, 14 through 20, 23A and 23B while the tag rivet and the tag receiver are held by the tray of FIGS. 8A through 12.

Referring now to FIGS. 24A and 24B, FIG. 24A is a front view of the applicator 52 engaged with both the tag rivet 8 and the tag receiver 10, wherein the tag rivet 8 is interference fit into the rivet recess 100 and the tag receiver 10 is interference fit into the receiver recess 96. FIG. 24B is a perspective side view of the applicator 52 positioned as shown in front view of FIG. 24A.

Referring now to FIGS. 25A and 25B, FIG. 25A is a front view of the applicator 52 positioned proximate to the ear 6, wherein the rivet jaw 102 is located higher in the Y dimension above the ear 6 and the receiver jaw 98 is positioned lower in the Y dimension relative to the ear 6. The rivet recess 100 includes a first rivet recess wall 100.A, a second rivet recess wall 100.B, a first rivet recess ledge 100.C and a second rivet recess ledge 100.D.

The first rivet recess wall 100.A extends in the Y dimension in a magnitude in the range of from 0.040 inches to 0.030 inches and in the Z dimension in a magnitude in the range from 0.190 inches to 0.210 inches. The second rivet recess wall 100.B extends in the Y dimension in a magnitude in the range of from 0.040 inches to 0.030 inches and in the Z dimension in a magnitude in the range from 0.190 inches to 0.210 inches. The first rivet wall 100.A and the second rivet wall 100.B are separated at a distance along the X dimension to provide an interference fit with the tag rivet 8.

The first rivet recess ledge 100.C extends in the X dimension in a magnitude in the range of from 0.040 inches to 0.070 inches and in the Z dimension in a magnitude in the range from 0.190 inches to 0.210 inches.

The second rivet recess ledge 100.D extends in the X dimension in a magnitude in the range of from 0.040 inches to 0.070 inches and in the Z dimension in a magnitude in the range from 0.190 inches to 0.210 inches.

The receiver recess 96 includes a first receiver recess wall 96.A, a second receiver recess wall 96.B, a first receiver recess ledge 96.C and a second receiver recess ledge 96.D.

The first receiver recess wall 96.A extends in the Y dimension in a magnitude in the range of from 0.040 inches to 0.030 inches and in the Z dimension in a magnitude in the range from 0.190 inches to 0.210 inches. The second receiver recess wall 96.B extends in the Y dimension in a magnitude in the range of from 0.040 inches to 0.030 inches and in the Z dimension in a magnitude in the range from 0.190 inches to 0.210 inches. The first receiver wall 96.A and the second receiver wall 96.B are separated at a distance along the X dimension to provide an interference fit with the tag receiver 10.

The first receiver recess ledge 96.C extends in the X dimension in a magnitude in the range of from 0.040 inches to 0.070 inches and in the Z dimension in a magnitude in the range from 0.190 inches to 0.210 inches.

The second receiver recess ledge 96.D extends in the X dimension in a magnitude in the range of from 0.040 inches to 0.070 inches and in the Z dimension in a magnitude in the range from 0.190 inches to 0.210 inches.

Figures 26A, 26B:
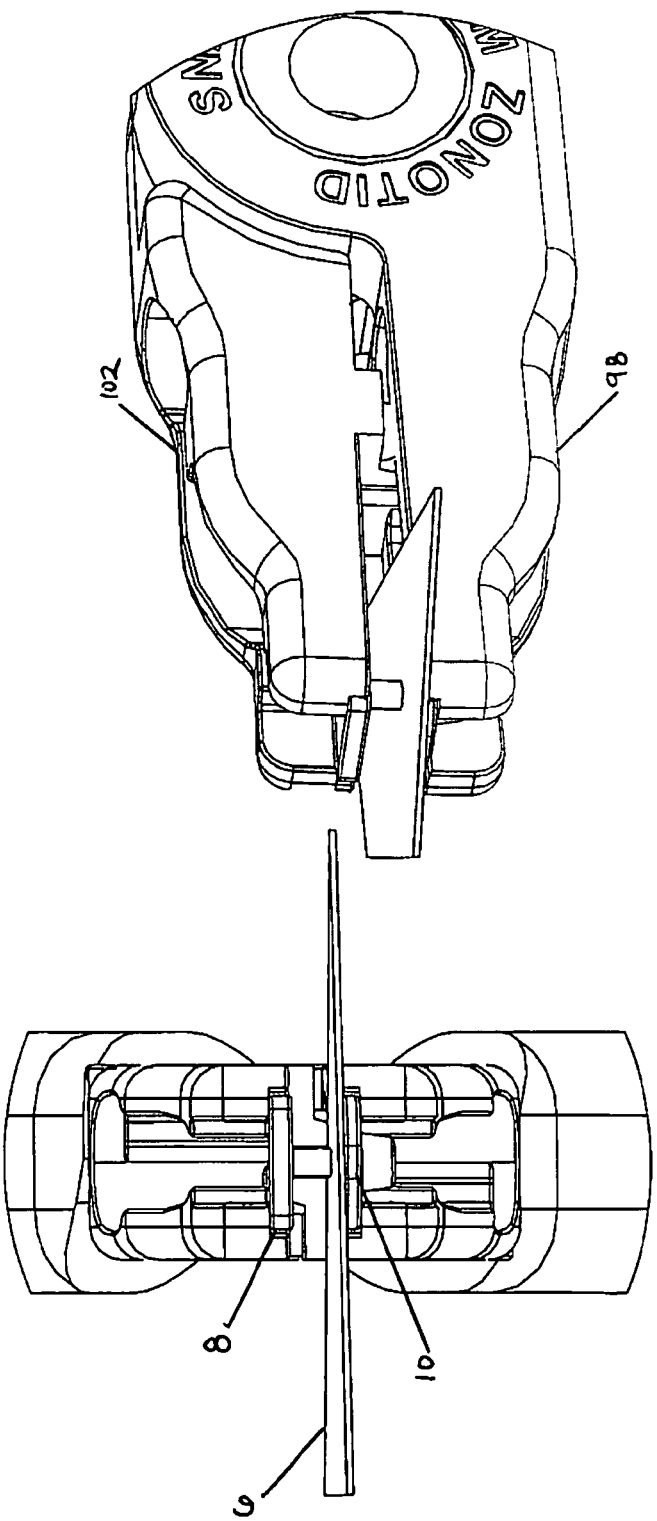
FIG. 26A is a front view of the applicator of FIGS. 12 through 21, 25A and 25B wherein the rivet post of FIGS. 1 through 8, 11, 12, 14 through 20, and 23 through 25B is piercing the ear of FIGS. 3, 4, 18, 19, 20, 25A and 25B.
FIG. 26B is a perspective view of the applicator of FIGS. 12 through 21 and FIGS. 25A through 26A, wherein the rivet post of FIGS. 1 through 8, 11, 12, FIGS. 14 through 20.

Referring now to FIGS. 26A and 26B, FIG. 26A is a front view of the applicator 52 wherein the rivet post 16 is piercing the ear 6 and the rivet post cutting tip 26 is fully inserted into the protective channel 36. FIG. 26B is a perspective side view of the applicator 52 in the same position as the front view of FIG. 26A.

FIG. 27A is a front view of the applicator 52 wherein the rivet jaw 102 and the receiver jaw 98 are being pressed together by a compressing force delivered along the Y axis by the user to the first handle 104 and the second handle 106.

The delivery of compressing forces along the Y dimension by the user are translated to forces to the upper angled post 120 and the lower angled post 118 along the Y dimension, thereby causing the receiver jaw 98 to splay laterally along the X dimension and thereby cause the separation between the first receiver recess wall 96.A and the second receiver wall 96.B of the receiver recess 96 to increase beyond 0.200 inches. The interference fit of the receiver 10 into the receiver recess 96 is thus terminated as the width of the receiver recess 96 along the X dimension is extended beyond the cross-sectional side length of the receiver plate 28, and the receiver 10 is thus no longer coupled with the receiver jaw 98 when the applicator 52 as shown in FIG. 27A.

This translation of forces to the upper angled post 120 and the lower angled post 118 along the Y dimension referred to in the preceding paragraph, thereby causing the rivet jaw 102 to splay laterally along the X dimension and thereby cause the separation between the first rivet recess wall 100.A and the second rivet wall 100.B of the rivet recess 100 to increase beyond 0.200 inches. The interference fit of the rivet 8 into the rivet recess 100 is thus terminated as the width of the rivet recess along the X dimension is extended beyond the cross-sectional side length of the rivet plate 14 and the rivet 8 is thus no longer coupled with the rivet jaw 102 when the applicator 52 as shown in FIG. 27A.

As shown on FIGS. 27A and 27B, the pair of raised stops 108 & 110 located respectively on the rivet jaw 102 and receiver jaw 98 are limiting the closing travel of the jaws 98 & 102 of the applicator 52 along the Y dimension so that the rivet 8 and the receiver 10 cannot over engage and potentially damage the rodent ear 6 or the first tag 2 itself.

FIG. 27B is a perspective view of the applicator 52 as positioned in the front view of FIG. 27A.

Figure 28:
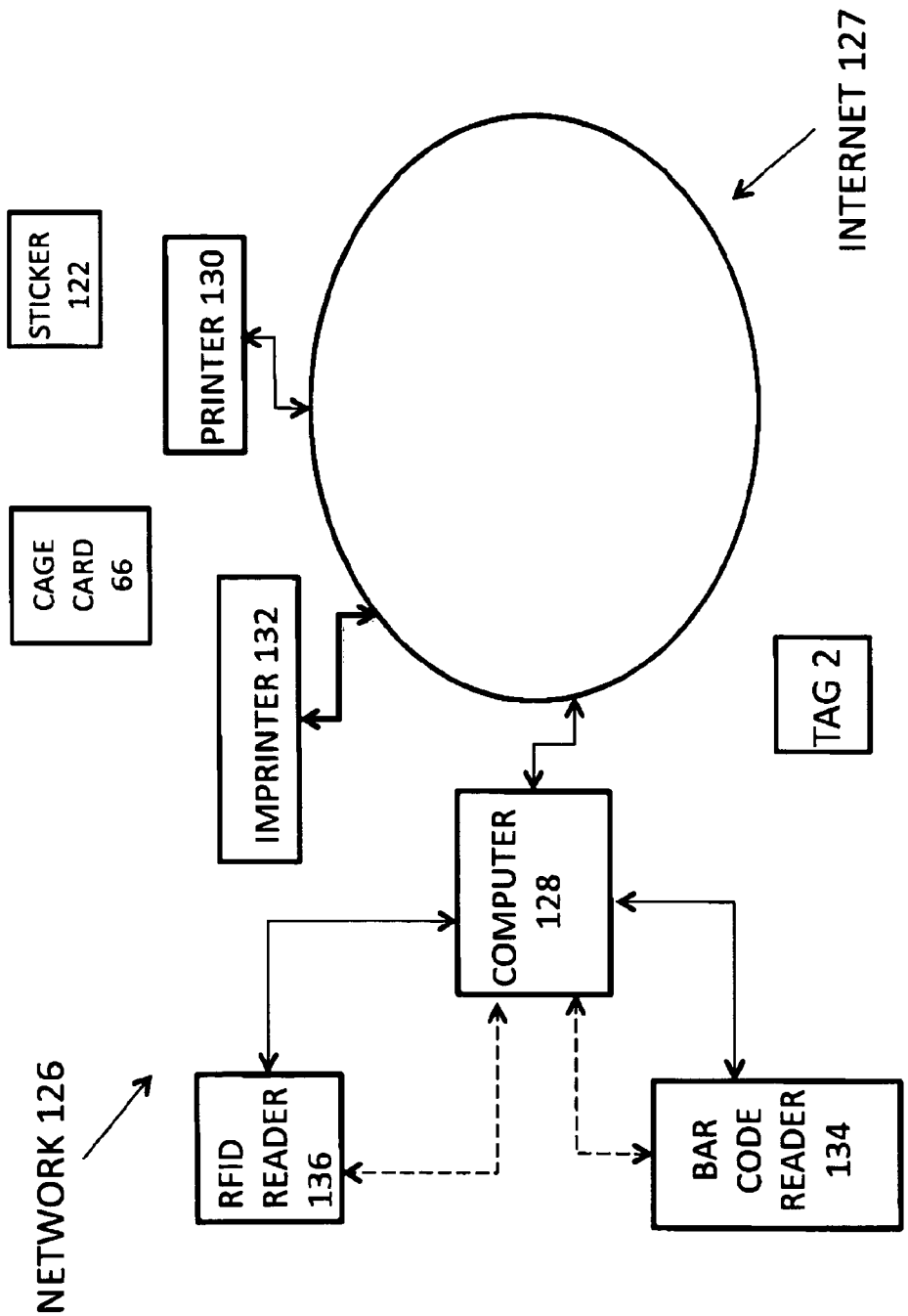
FIG. 28 is a schematic illustration of an electronic communications network comprising of a computational system and additional associated equipment useful to use, monitor and automatically read and decode the tag of FIGS. 1 through 8, 11, 12, FIGS. 14 through 20, and FIGS. 23A through 27B.

Referring now to FIG. 28, FIG. 28 is a schematic illustration of an electronic communications network 126 comprising a computational system 128 and additional associated equipment useful to use, monitor and automatically read the first tag 2. The electronic communications network 126, or network 126, may be or comprise the Internet 127, a wireless communications network, a telephony network, and/or a cellular telephone network.

The computational system 128, or network computer 128, is bi-directionally communicatively coupled with the network 126 and may be selected from a group of suitable electronic devices known in the art, including (1.) a Nokia Model E61™ cellular telephone marketed by Nokia Corporation of Espoo Finland; (2.) a BLACKBERRY™ wireless personal digital assistant 20 marketed by Research-in-Motion of Waterloo, Ontario, Canada; (3.) a VAIO FS8900™ notebook computer marketed by Sony Corporation of America, of New York City, N.Y.; (4.) POWERBOOK G4™ personal computer marketed by Apple Computer, Inc., of Cupertino, Calif.; or (5.) an iPhone™ cellular telephone marketed by Apple Computer, Inc., of Cupertino, Calif.

A network-enabled printer 130 is communicatively coupled to the network 126 and is configured to print the bar code 58, the color code 62, and/or the alphanumeric code 60 onto the cage card 66 and the sticker 122. The printer 130 may be a Konica Minolta Model Bizhub C456™ printer as marketed by Minolta Corporation of Tokyo, Japan. The network enabled imprinter 132 is communicatively coupled to the network 126 and is configured to mark, laser mark imprint, and/or etch the bar code 58, the color code 62, and/or the alphanumeric code 60 onto rivet display plate 18.

A bar code reader 134 is configured to read the bar code 58 from the rivet display plate 18, the cage card 66 and the sticker 122 and communicate information read from, or derived from the information read from, the rivet display plate 18, the cage card 66 or the sticker 122 to the computer 128 by a wired connection or a wireless communication. It is understood that the solid line extending from the computer 128 and to the bar code reader 134 represents a wired communication connection and that the dashed line extending from the computer 128 and to the bar code reader 134 represents a wireless communications connection. The bar code reader 134 may be (a.) a Code Reader CR1200™ bar code scanner marketed by Code Corporation of Bluffdale, Utah; (b.) a 4600g Scanner™ bar code scanner marketed by Honeywell Corporation of Morristown, N.J.; (c.) a Gryphon™ bar code scanner marketed by Datalogic Scanning, Inc. of Greeneville, S.C.; or (d.) other suitable bar code scanner known in the art.

An RFID reader 136 is configured to receive a wireless radio wave transmission from the RFID 12 of the first tag 2. The RFID reader 12 may further be configured to provide electrical power via radio wave transmission to the RFID 12. The RFID reader 136 is further configured to communicate information read from, or derived from the information read from, the RFID 12 by a wired connection or a wireless communication. It is understood that the solid line extending from the computer 128 and to the RFID reader 136 represents a wired communication connection and that the dashed line extending from the computer 128 and to the RFID code reader 136 represents a wireless communications connection.

Figure 29:
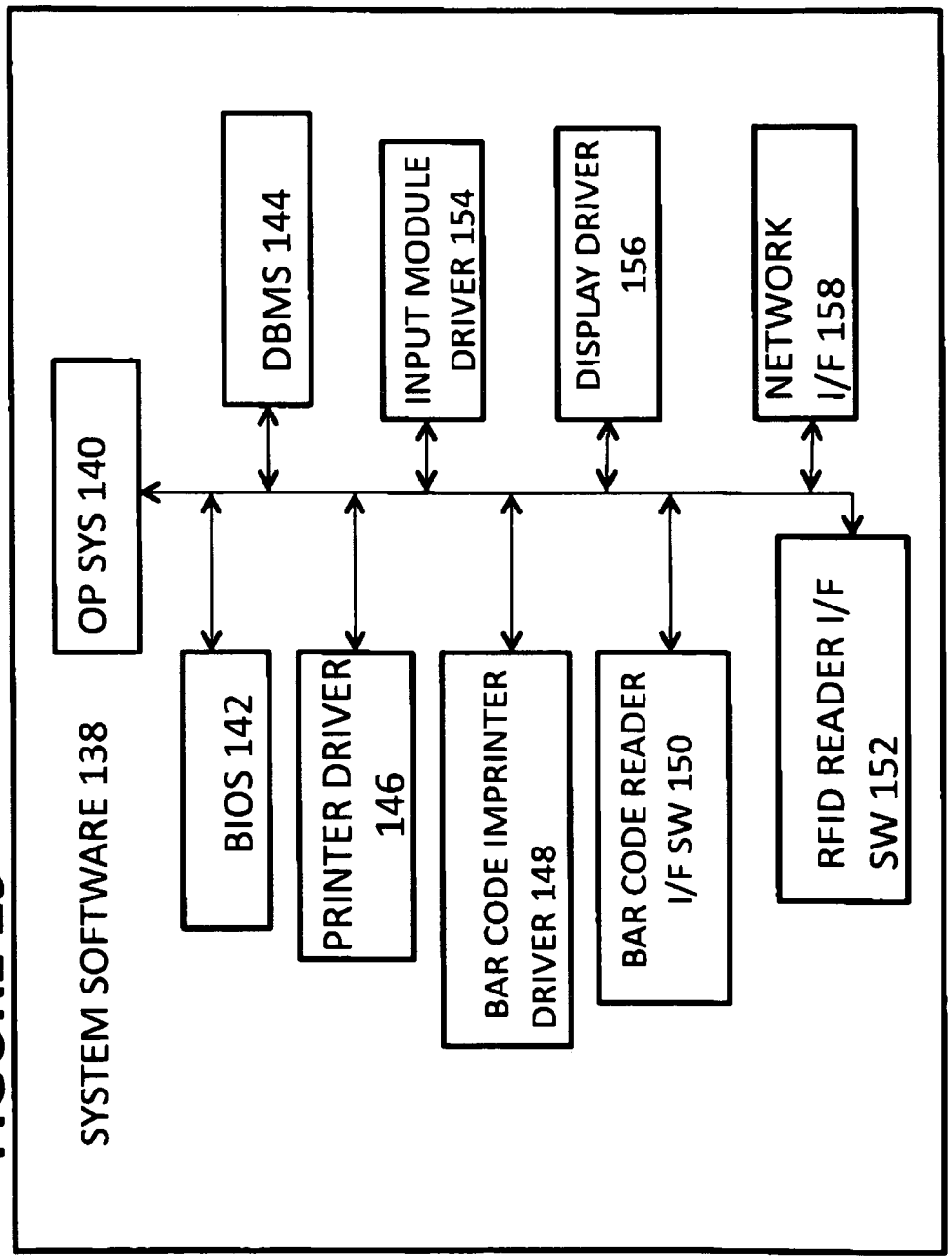
FIG. 29 is a schematic of the software of the computational system of FIG. 28.

Referring now to FIG. 29, FIG. 29 is a schematic of a system software 138 of the computer 128. The system software includes an operating system software 140, a basic input/output system 142, a data base management system 144, a printer driver software 146, a bar code imprinter driver 148, a bar code reader interface software 150, an RFID reader interface software 152, an input module software 154, a display driver software 156, and a network communications software 158. The operating system 140 enables the computer 128 to contemporaneously run or execute the other software modules 142-158 as directed by the user. The basic input/output system 142 enables the computer 128 to boot-up upon command by the user.

The data base management system 144, or DBMS 144, may be or comprise (1.) an object oriented database and an Object Oriented DBMS, (2.) an IBM DB2 Universal Database™ server (in Linux, UNIX®) marketed by IBM Corporation of Armonk, N.Y.; (3.) WINDOWS™ operating system environments marketed by Microsoft Corporation of Redmond, Wash.; (4.) a relational database, such as an SQL Server Yukon™ relational database software as marketed by Microsoft Corporation of Redmond, Wash.; (5.) an Oracle Database 11g™ relational database software as marketed by Oracle Corporation of Redwood Shores, Calif.; and/or (6.) other suitable DBMS known in the art.

The printer driver software 146 enables the computer 128 to instruct the printer 130 to print the bar code 58, the color code 62, and/or the alphanumeric code 60 onto the cage card 66 and the sticker 122. The bar code imprinter driver 148 146 enables the computer 128 to instruct the imprinter 132 to mark, laser mark imprint, and/or etch the bar code 58, the color code 62, and/or the alphanumeric code 60 onto rivet display plate 18. The bar code reader interface software 150 enables the computer 128 to receive information from the bar code reader 134. The RFID reader interface software 152 enables the computer 128 to receive information transmitted from the RFID 136.

The input module software 154 enables the computer 128 to receive commands and information provided by the user via an input device of the computer, e.g., a computer keyboard. The display driver software 156 enables the computer 128 to direct a display module of the computer 128, e.g., an electronic display screen, to present visual representations of information. The network communications software 158 enables the computer 128 to bi-directionally communicate with and via the network 126.

The foregoing disclosures and statements are illustrative only of the present invention, and are not intended to limit or define the scope of the present invention. The above description is intended to be illustrative, and not restrictive. Although the examples given include many specificities, they are intended as illustrative of only certain possible applications of the present invention. The examples given should only be interpreted as illustrations of some of the applications of the present invention, and the full scope of the Present Invention should be determined by the appended claims and their legal equivalents. Those skilled in the art will appreciate that various adaptations and modifications of the just-described applications can be configured without departing from the scope and spirit of the present invention. Therefore, it is to be understood that the present invention may be practiced other than as specifically described herein. The scope of the present invention as disclosed and claimed should, therefore, be determined with reference to the knowledge of one skilled in the art and in light of the disclosures presented above.

We claim:

1. A kit comprising:
   a display rivet comprising
     a rivet plate and a rivet post,
     the rivet plate defining an optically-encoded surface, a straight edge adjacent the optically-encoded surface, and a first posterior surface, and
     the rivet post extending from the first posterior surface, defining a cutting tip distal the rivet plate, and defining a neck between the cutting tip and the rivet plate;
   a receiver defining a second posterior surface and a channel coincident the second posterior surface and configured to receive the rivet post;
   a tray comprising:
     a rivet aperture configured to retain the display rivet,
     an alignment structure configured to mate with the straight edge and to constrain the display rivet about an axis of the rivet post, and
     a receiver aperture configured to retain the receiver with the channel substantially aligned with the post and the second posterior surface adjacent and offset the first posterior surface by a first distance; and
   an applicator comprising a first jaw and a second jaw and operable in a first position, a second position, and a third position;
   wherein, in the first position, the first jaw engages the rivet plate retained by the rivet aperture and the second jaw engages the receiver retained by the receiver aperture;
   wherein the first jaw and the second jaw transition from the first position into the second position to separate the rivet plate and the receiver from the tray; and
   wherein the first jaw and the second jaw transition from the second position into the third position to insert the post into the channel with the neck retaining the receiver and the first posterior surface adjacent and offset the second posterior surface by a second distance less than the first distance; wherein the rivet plate comprises a rectangular section defining the optically-encoded surface; wherein the alignment structure comprises ledge defining planar face offset from the rivet aperture and configured to constrain the rivet date in rotation about the rivet post to an approach angle less than eight degrees from the planar face of the ledge by contacting a side of the rivet plate.

2. The kit of claim 1, wherein the rectangular section of the rivet plate is approximately square in cross-section; and wherein the optically-encoded surface comprises a square two-dimensional optically encoded image.

3. The kit of claim 2, wherein the first jaw comprises:
   a left jaw face defining a left planar surface;
   a right jaw face defining a right planar face opposing and parallel to the left jaw face;
   a rear stop adjacent and perpendicular to the left jaw face and the right jaw face;
   an opening opposite the rear stop; and
   an upper stop arranged over and extending inwardly from the left jaw face and the right jaw face.

4. The kit of claim 1, further comprising a second display rivet comprising a second rivet plate defining a second straight edge; wherein the tray comprises a second rivet aperture; and wherein the alignment structure constrains the straight edge of the display rivet substantially parallel to the second straight edge of the second display rivet when the display rivet and the second display rivet are installed in the rivet aperture and in the second rivet aperture of the tray.

5. The kit of claim 4, wherein the alignment structure comprises a unitary ledge extending along a top of the tray adjacent the rivet aperture and the second rivet aperture.

6. The kit of claim 1,
   wherein the tray defines:
     a first row of rivet apertures comprising the rivet aperture;
     a first row of receiver apertures below the first row of rivet apertures and comprising the receiver aperture;
     a second row of rivet apertures in-plane with the first row of rivet apertures; and
     a second row of receiver apertures below the second row of rivet apertures; and
   wherein the alignment structure comprises a ledge interposed between and extending along the first row of rivet apertures and the second row of rivet apertures.

7. The kit of claim 6, wherein the tray is configured to receive a set of display rivets in the first row of rivet apertures and in the second row of rivet apertures with tops of each rivet plate in the set of display rivets accessible from above the tray; wherein the set of display rivets comprises the display rivet; and wherein the top of each rivet plate in the set of display rivets is etched with a unique encoded optical identifier while installed in the tray.

8. The kit of claim 7, wherein the rivet plate comprises a metal element; and wherein the metal element is laser-etched with a unique two-dimensional optically encoded image while the display rivet is installed in the rivet aperture of the tray.

9. The kit of claim 7, wherein a first rivet aperture and a second rivet aperture in the first row of rivet apertures are offset by at least a width of one side of the first jaw of the applicator.

10. The kit of claim 1, wherein the applicator comprises a stop defining a minimum distance between the first jaw and the second jaw in the third position, the minimum distance greater than a thickness of a rodent ear.

11. The kit of claim 10, wherein the first jaw of the applicator comprises a first split jaw comprising a first post; and wherein the stop splays the first split jaws laterally by engaging the first post in order to release the display rivet from the first jaw when the applicator reaches the third position.

12. The kit of claim 11, wherein the first jaw comprises an upper stop that contacts the display rivet adjacent the optically-encoded surface of the display rivet and that depresses the display rivet toward the receiver as the stop splays the first jaw laterally during transition from the second position to the third position.

13. A kit comprising:
- a set of display rivets, each display rivet in the set of display rivets comprising:
  - a rivet plate defining an optically-encoded surface, an straight edge adjacent the optically-encoded surface, and a first posterior surface; and
  - a rivet post extending from the first posterior surface, defining a cutting tip distal the rivet plate, and defining a neck between the cutting tip and the rivet plate;
- a set of receivers, each receiver in the set of receivers defining:
  - a second posterior surface; and
  - a channel coincident the second posterior surface and configured to receive a rivet post of a display rivet;
- a tray comprising:
  - a linear row of rivet apertures, each rivet aperture in the linear row of rivet apertures configured to retain the display rivet,
  - a linear row of receiver apertures, each receiver aperture in the linear row of receiver apertures arranged below a corresponding rivet aperture in the linear row of rivet apertures and configured to retain a receiver in the set of receivers with the channel of the receiver substantially aligned with a post of a corresponding display rivet and with the second posterior surface of the receiver adjacent and offset the first posterior surface of the display rivet by a first distance; and
  - a ledge extending along the row of rivet apertures and configured to mate with the straight edge of each display rivet arranged in a rivet aperture in the linear row of rivet apertures to constrain each display rivet in rotation about the rivet post to a limited range of approach angles; and
- an applicator comprising a first jaw and a second jaw and operable in:
  - a first position to engage a particular display rivet and a corresponding particular receiver installed in the tray in the first jaw and in the second jaw;
  - a second position to remove the particular display rivet and the particular receiver from the tray; and
  - a third position to insert a post of the particular display rivet into a channel of the particular receiver;
- wherein each display rivet comprises a rectangular section defining an optically-encoded surface; and
- wherein the ledge defines a planar face offset from the linear row of rivet apertures and configured to constrain each display rivet, installed in a rivet aperture in the linear row of rivet apertures, in rotation about a rivet post to an approach angle less than eight degrees from the planar face of the ledge by contacting a side of the rivet plate.

14. The kit of claim 13,
- wherein, in the first position, the first jaw engages the rivet plate of a particular display rivet, in the set of display rivets, retained by a rivet aperture and the second jaw engages a corresponding particular receiver, in the set of receivers, retained by a receiver aperture;
- wherein the first jaw and the second jaw transition from the first position into the second position to separate the particular rivet plate and the particular receiver from the tray; and
- wherein the first jaw and the second jaw transition from the second position into the third position to insert a post of the particular display rivet into a channel of the particular receiver with a neck of the post retaining the particular receiver and a first posterior surface of the particular display rivet adjacent and offset a second posterior surface of the particular receiver by a second distance less than the first distance.

15. The kit of claim 13, wherein the tray is configured to receive the set of display rivets in the linear row of rivet apertures with tops of each display rivet in the set of display rivets accessible from above the tray; and wherein the top of each display rivet in the set of display rivets is etched with a unique encoded optical identifier while installed in the tray.

16. The kit of claim 15, wherein each display rivet in the set of display rivets comprises a metal element; and wherein the metal element of each display rivet in the set of display rivets is laser-etched with a unique two-dimensional optically encoded image while the display rivet is installed in a rivet aperture of the tray.

17. The kit of claim 13, wherein the applicator comprises a stop defining a minimum distance between the first jaw and the second jaw in the third position, the minimum distance greater than a thickness of a rodent ear.

18. The kit of claim 17, wherein the first jaw of the applicator comprises a first split jaw comprising a first post; wherein the stop splays the first split jaws laterally by engaging the first post in order to release the display rivet from the first jaw when the applicator reaches the third position; and wherein the first jaw comprises an upper stop that contacts an optically-encoded surface of a display rivet and that depresses the optically-encoded surface of the display rivet toward a corresponding receiver as the stop splays the first jaw laterally during transition from the second position to the third position.

* * * * *